United States Patent
Curran

(10) Patent No.: US 12,042,264 B2
(45) Date of Patent: Jul. 23, 2024

(54) SYSTEM FOR MEASURING IMPEDANCE BETWEEN A PLURALITY OF ELECTRODES OF A MEDICAL DEVICE

(71) Applicant: St. Jude Medical, Cardiology Division, Inc., St. Paul, MN (US)

(72) Inventor: Timothy G. Curran, St. Paul, MN (US)

(73) Assignee: ST. JUDE MEDICAL, CARDIOLOGY DIVISION, INC., St. Paul, MN (US)

(*) Notice: Subject to any disclaimer, the term of this patent is extended or adjusted under 35 U.S.C. 154(b) by 5 days.

(21) Appl. No.: 17/884,758

(22) Filed: Aug. 10, 2022

(65) Prior Publication Data
US 2023/0077196 A1    Mar. 9, 2023

Related U.S. Application Data

(63) Continuation of application No. 16/930,905, filed on Jul. 16, 2020, now Pat. No. 11,439,319, which is a
(Continued)

(51) Int. Cl.
*A61B 5/06* (2006.01)
*A61B 5/00* (2006.01)
(Continued)

(52) U.S. Cl.
CPC .............. *A61B 5/063* (2013.01); *A61B 5/053* (2013.01); *A61B 5/0538* (2013.01); *A61B 5/282* (2021.01);
(Continued)

(58) Field of Classification Search
CPC ....... A61B 5/063; A61B 5/053; A61B 5/0538; A61B 5/282; A61B 5/6852; A61B 5/6856;
(Continued)

(56) References Cited

U.S. PATENT DOCUMENTS

| 4,587,975 A | 5/1986 | Salo et al. |
| 5,341,807 A | 8/1994 | Nardella |

(Continued)

FOREIGN PATENT DOCUMENTS

| CN | 101534736 A | 9/2009 |
| CN | 102355856 A | 2/2012 |

(Continued)

OTHER PUBLICATIONS

"Notice of Decision to Grant Received mailed on Apr. 22, 2023", 4 Pages.
(Continued)

*Primary Examiner* — Akm Zakaria
(74) *Attorney, Agent, or Firm* — Billion & Armitage

(57) ABSTRACT

The present disclosure is directed to measuring impedance across a plurality of electrode pairs. The disclosed systems and methods may simultaneously provide drive signals between electrode pairs and then sense the voltage signals that develop at the electrodes. Digital signal processing may be used to synchronously demodulate the voltage signal at each electrode to determine impedances at the electrodes. Each electrode pair may be driven at a unique frequency to allow for significantly increasing a number of electrode pairs and/or increasing drive current magnitudes. Synchronous demodulation allows the unique frequencies to be detected independent of each other while minimizing crosstalk. Typically, the drive frequencies are made orthogonal by setting the drive frequencies at harmonics of a common base frequency and measuring a response over an integer number of cycles. In an embodiment, quadrature demodulation may occur providing a real component for resistive impedance and an imaginary component for reactive impedance.

20 Claims, 13 Drawing Sheets

Related U.S. Application Data continuation of application No. 16/168,423, filed on Oct. 23, 2018, now Pat. No. 10,750,974.

(60) Provisional application No. 62/576,447, filed on Oct. 24, 2017.

(51) Int. Cl.
| | |
|---|---|
| *A61B 5/053* | (2021.01) |
| *A61B 5/0538* | (2021.01) |
| *A61B 5/282* | (2021.01) |
| *A61B 18/00* | (2006.01) |
| *A61B 18/12* | (2006.01) |
| *A61B 18/14* | (2006.01) |
| *A61B 34/20* | (2016.01) |

(52) U.S. Cl.
CPC .......... *A61B 5/6852* (2013.01); *A61B 5/6856* (2013.01); *A61B 5/7225* (2013.01); *A61B 18/1492* (2013.01); *A61B 34/20* (2016.02); *A61B 5/068* (2013.01); *A61B 5/7221* (2013.01); *A61B 2018/0016* (2013.01); *A61B 2018/00267* (2013.01); *A61B 2018/00351* (2013.01); *A61B 2018/00577* (2013.01); *A61B 2018/00839* (2013.01); *A61B 2018/00845* (2013.01); *A61B 2018/00875* (2013.01); *A61B 2018/00892* (2013.01); *A61B 2018/128* (2013.01); *A61B 2018/1435* (2013.01); *A61B 2034/2053* (2016.02); *A61B 2562/0209* (2013.01)

(58) Field of Classification Search
CPC ... A61B 5/7225; A61B 18/1492; A61B 34/20; A61B 5/068; A61B 5/7221; A61B 2018/0016; A61B 2018/00267; A61B 2018/00351; A61B 2018/00577; A61B 2018/00839; A61B 2018/00845; A61B 2018/00875; A61B 2018/00892; A61B 2018/128; A61B 2018/1435; A61B 2034/2053; A61B 2562/0209
See application file for complete search history.

(56) References Cited

U.S. PATENT DOCUMENTS

| | | | |
|---|---|---|---|
| 5,469,857 A | 11/1995 | Laurent et al. | |
| 5,836,990 A | 11/1998 | Li | |
| 6,129,669 A | 10/2000 | Panescu et al. | |
| 6,391,024 B1 | 5/2002 | Sun et al. | |
| 6,471,693 B1 | 10/2002 | Carroll et al. | |
| 6,546,270 B1 | 4/2003 | Goldin et al. | |
| 6,569,160 B1 | 5/2003 | Goldin et al. | |
| 7,263,397 B2 | 8/2007 | Hauck et al. | |
| 8,160,690 B2 | 4/2012 | Wilfley et al. | |
| 8,369,922 B2 | 2/2013 | Paul et al. | |
| 8,403,925 B2 | 3/2013 | Miller et al. | |
| 8,406,866 B2 | 3/2013 | Deno et al. | |
| 8,672,936 B2 | 3/2014 | Thao et al. | |
| 9,687,289 B2 | 6/2017 | Govari et al. | |
| 9,750,570 B2 | 9/2017 | Condie et al. | |
| 9,901,386 B2 | 2/2018 | Wham et al. | |
| 10,384,062 B2 | 8/2019 | Chang et al. | |
| 2004/0230131 A1 | 11/2004 | Kassab et al. | |
| 2007/0043303 A1 | 2/2007 | Osypka et al. | |
| 2007/0060833 A1 | 3/2007 | Hauck | |
| 2007/0123764 A1 | 5/2007 | Thao et al. | |
| 2008/0269631 A1 | 10/2008 | Denison et al. | |
| 2008/0275442 A1 | 11/2008 | Paul et al. | |
| 2008/0312713 A1 | 12/2008 | Wilfley et al. | |
| 2009/0158852 A1 | 6/2009 | Paul et al. | |
| 2010/0010612 A1 | 1/2010 | Gelbart et al. | |
| 2010/0168560 A1 | 7/2010 | Hauck et al. | |
| 2010/0217132 A1 | 8/2010 | Ellingwood et al. | |
| 2011/0306867 A1 | 12/2011 | Gopinathan et al. | |
| 2012/0078342 A1 | 3/2012 | Vollkron et al. | |
| 2012/0116387 A1 | 5/2012 | Govari et al. | |
| 2012/0172702 A1 | 7/2012 | Koyrakh et al. | |
| 2012/0203169 A1 | 8/2012 | Tegg | |
| 2012/0238897 A1 | 9/2012 | Wilfley et al. | |
| 2013/0331674 A1 | 12/2013 | Yang et al. | |
| 2014/0364715 A1 | 12/2014 | Hauck | |
| 2015/0157240 A1* | 6/2015 | Shoudy ............... | A61B 5/0536 600/547 |
| 2015/0285887 A1 | 10/2015 | Bollenbeck | |
| 2016/0184004 A1 | 6/2016 | Hull et al. | |
| 2016/0242667 A1 | 8/2016 | Fay et al. | |
| 2016/0287136 A1 | 10/2016 | Condie et al. | |
| 2016/0339239 A1 | 11/2016 | Yoo et al. | |
| 2017/0007157 A1* | 1/2017 | Gross .................... | A61B 5/068 |
| 2020/0113523 A1* | 4/2020 | Osypka ............... | A61B 5/0535 |

FOREIGN PATENT DOCUMENTS

| | | |
|---|---|---|
| CN | 204971565 U | 1/2016 |
| CN | 105338885 A | 2/2016 |
| CN | 106999084 A | 8/2017 |
| EP | 1169976 A1 | 1/2002 |
| EP | 1962945 B1 | 4/2016 |
| JP | 2006501903 A | 1/2006 |
| JP | 2016524480 A | 8/2016 |
| JP | 2016187720 A | 11/2016 |
| WO | 0078239 A2 | 12/2000 |
| WO | 2010020958 A1 | 2/2010 |
| WO | 2011060497 A1 | 5/2011 |
| WO | 2013162884 A1 | 10/2013 |
| WO | 2016081650 A1 | 5/2016 |
| WO | 2016081786 A1 | 5/2016 |
| WO | 2016153561 A1 | 9/2016 |

OTHER PUBLICATIONS

Assambo, C., "Determination of the Parameters of the Skin-Electrode Impedance Model for ECG Measurement," Proceedings of the 6th WSEAS Int. Conf. on Electronics, Hardware, Wireless and Optical Communications, pp. 90-95, Feb. 2007.

International Search Report for International Application No. PCT/US2018/066384, dated Apr. 11, 2019.

"Extended European Search Report Received mailed Aug. 6, 2021", Aug. 6, 2021, 9 pages.

* cited by examiner

SYSTEM FOR MEASURING IMPEDANCE BETWEEN A PLURALITY OF ELECTRODES OF A MEDICAL DEVICE

CROSS-REFERENCE TO RELATED APPLICATIONS

This application is a continuation of U.S. patent application Ser. No. 16/930,905, filed Jul. 16, 2020, which is a continuation of U.S. patent application Ser. No. 16/168,423, filed Oct. 23, 2018, now U.S. Pat. No. 10,750,974, which claims the benefit of U.S. Provisional Application No. 62/576,447, filed Oct. 24, 2017, both of which are incorporated by reference in their entirety.

BACKGROUND a. Technical Field

The instant disclosure relates to electrical impedance-based measurement of electrodes of a medical device to determine, among other things, contact between tissue and the electrodes of the medical device. More specifically, the disclosure relates to digital signal processing to simultaneously detect impedance on multiple electrodes while maintaining safe current limits for a patient.

b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site such as, for example, a site within the patient's heart. The catheter typically carries one or more electrodes, which may be used for ablation, diagnosis, and the like.

In many procedures, it may be beneficial to know the contact status of an electrode (e.g., in contact with tissue, in a blood pool) on a catheter. For example, in an electrophysiology mapping procedure, the electrical signal present on an electrode may vary depending on whether the electrode is in contact with tissue, or adjacent to the tissue in a blood pool, and that difference may be accounted for in software. In another example, in an ablation procedure, it may be desirable to only drive an ablation current when an electrode is in contact with the tissue to be ablated.

One existing methodology that may be used to determine whether an electrode on a catheter is in contact with tissue includes driving a current between the electrode and an electrode elsewhere within the patient (e.g., at a stable position within the patient) or on the exterior of the patient (e.g., on the patient's skin) and assessing the impedance between the electrodes. To determine an impedance between those electrodes, the electric potential of the electrode on the medical device may be referenced to a third electrode, which may also be elsewhere within the patient or on the exterior of the patient.

The foregoing discussion is intended only to illustrate the present field and should not be taken as a disavowal of claim scope.

BRIEF SUMMARY

In one embodiment, a system, such as an electronic control unit, is provided for measuring impedances between electrodes of a connected medical device. The system may include a controller or frequency source configured to generate a plurality of drive signals. Each of the drive signals may have a unique modulation frequency that is a harmonic of a common base frequency. The controller or frequency source may further be configured to simultaneously apply each of the plurality of drive signals across an individual pair of electrodes of the connected medical device. The medical device may be a catheter, however, the system is not limited to use with catheters and may be utilized with other medical devices. The system may include a measurement circuit for measuring responses of the drive signals as applied to individual pairs of electrodes of the medical device. A demodulator is configured simultaneously demodulate the response signal(s) (e.g., a composite response signal) for each unique modulation frequency. The demodulator may generate demodulation signals each having an identical frequency to one unique modulation frequency and known phase that is different than a phase of the unique modulation frequency. Such demodulation may include quadrature demodulation to provide resistive impedance information and reactive impedance information for each electrode. In an embodiment, the demodulator samples over a sampling period having an integer number of cycles for the common base frequency. Impedance information may be output for each of the electrodes.

In a further arrangement, the system is a digital signal processing system where the drive signals are digital drive signals. In such an arrangement, the digital drive signals are converted to analog signals by one or more digital-to-analog (DAC) converters prior application across the individual pairs of electrodes. Likewise, one or more analog-to-digital (ADC) converters may convert analog responses of the electrodes to digital response signals. In one arrangement, the plurality of drive signals or modulation signals having unique frequencies may be generated utilizing one or more numerically controlled oscillators (modulating NCOs). In such an arrangement, the plurality of demodulation signals may be generated utilizing one or more NCOs (demodulating NCOs). The modulating and demodulating NCOs may receive inputs identifying each unique modulation frequency and demodulation frequency, respectively. Additionally, corresponding modulating and demodulating NCOs may receive inputs identifying a phase offset. Such phase offsets may be random and may be assigned from stored calibration information. In an arrangement, the modulating and demodulating NCOs may be defined on a common field programmable gate array (FPGA). In such an arrangement, the controller and/or demodulator may also be defined in the FPGA.

In a further arrangement, the system may be configured to identify a number of individual pairs of electrodes for the medical device and adjust the current level of the drive signals based on the number of individual pairs of electrodes. In such an arrangement, the system may maintain a combined or sum current level for the drive signals below a predetermined threshold (e.g., auxiliary current level). In one arrangement, the system may maximize current level for the drive signals while maintaining the combined current level below the predetermined threshold.

In one embodiment, a method is provided for measuring impedances between electrodes of a connected medical device. The method may include generating a plurality of drive signals. Each of the drive signals may have a modulation frequency that is a harmonic of a common base frequency. The drive signals may each be simultaneously applied across an individual pair of electrodes of the medical device. The method may further include measuring a composite response signal of the plurality of drive signals applied to the plurality of individual pairs of electrodes. The composite response signal may be synchronously demodulated for each unique modulation frequency. Once demodulated, impedance values may be output for each electrode and/or each individual pair of electrodes. In an arrangement, the drive signals are made orthogonal. In another arrangement, the response signal is sampled over a sampling period having an integer number of cycles for the common base frequency.

In a further arrangement, the method includes identifying a number of electrode pairs of a medical device. In such an arrangement, the method may include adjusting a current level of the drive signals based on the identified number of electrode pairs. The current level may be adjusted to maximize a current level while maintaining a sum current level of the drive signals below a predetermined threshold.

Systems and methods according to the present disclosure may simultaneously provide drive signals between electrode pairs and then sense the voltage that develops at the electrodes. Digital signal processing synchronously demodulates the voltage signal at each electrode to determine impedances at the electrodes. Each electrode pair may be driven at a unique frequency to allow for significantly increasing a number of electrode pairs and/or increasing drive current magnitudes while minimizing crosstalk between channels. Synchronous demodulation may allow the unique frequencies to be detected independent of each other while minimizing crosstalk. To allow synchronous demodulation, the drive frequencies may be made orthogonal to each other by setting the drive frequencies at harmonics of a base frequency and measuring a response over a period with an integer number of cycles. In an embodiment, quadrature demodulation may occur providing a real component for resistive impedance and an imaginary component for reactive impedance.

Synchronous demodulation may also allow for signal extraction with very low drive current levels (e.g., 1 micro-amp-20 micro-amps). Further, in an embodiment, use of low drive current levels in conjunction with unique frequencies may allow for significantly increasing the number of electrodes excited while maintaining auxiliary current levels for a patient below a predetermined threshold. In an embodiment, fifty drive signals may be provided each having a drive current at or below about 20 micro-amps. In another embodiment, one-hundred drive signals may be provided each having a drive current at or below about 10 micro-amps. In a further embodiment, two hundred drive signals may be provided each having a drive current at or below about 5 micro-amps.

DETAILED DESCRIPTION

Figure 1:
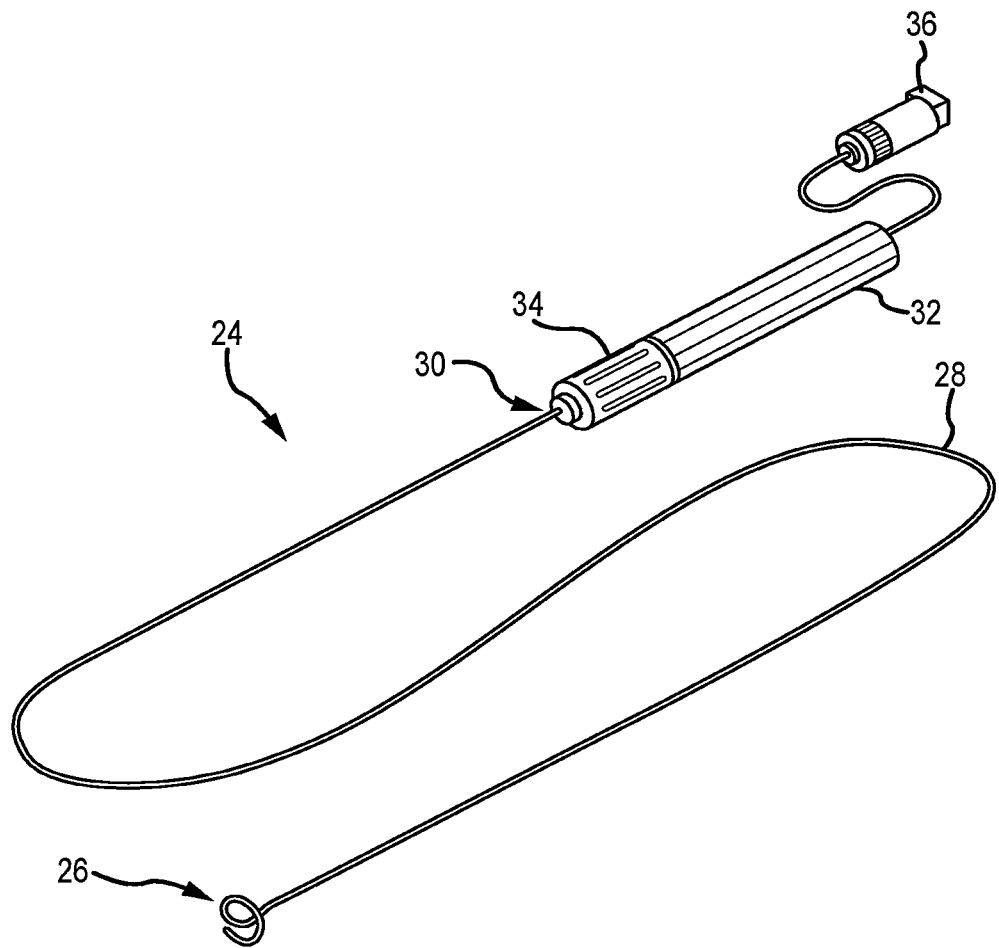
FIG. 1 is an isometric view of an exemplary embodiment of an elongate medical device having a distal lariat portion.

Referring now to the figures, in which like numerals indicate the same or similar elements in the various views, FIG. 1 is an isometric view of an exemplary embodiment of an elongate medical device 24. The elongate medical device 24 may comprise, for example, a diagnostic and/or therapy delivery catheter, an introducer or sheath, or other like devices. For purposes of illustration and clarity, the description below will be with respect to an embodiment where the elongate medical device 24 comprises a catheter (i.e., catheter 24). It will be appreciated, however, that embodiments wherein the elongate medical device 24 comprises an elongate medical device other than a catheter remain within the spirit and scope of the present disclosure.

Referring to FIG. 1, the catheter 24 may comprise a shaft 28 having a distal end portion 26 and a proximal end portion 30. The catheter 24 may be configured to be guided through and disposed in the body of a patient. Accordingly, the proximal end portion 30 of the shaft 28 may be coupled to a handle 32, which may include features to enable a physician to guide the distal end portion to perform a diagnostic or therapeutic procedure such as, for example only, an ablation or mapping procedure on the heart of the patient. Accordingly, the handle 32 may include one or more manual manipulation mechanisms 34 such as, for example, rotational mechanisms and/or longitudinal mechanisms, coupled to pull wires for deflecting the distal end portion of the shaft. Exemplary embodiments of manipulation mechanisms, pull wires, and related hardware are described, for example only, in U.S. patent application publication no. 2012/0203169, hereby incorporated by reference in its entirety. The handle 32 may further include one or more electromechanical connectors for coupling to a mapping and navigation system, an ablation generator, and/or other external systems. The handle 32 may also include one or more fluid connectors 36 for coupling to a source and/or destination of fluids such as, for example only, a gravity feed or fixed or variable-rate pump. Accordingly, the distal end portion 26 of the shaft 28 may also include one or more fluid ports or manifolds for distributing or collecting fluids such as, for example only, irrigation fluid during an ablation procedure. The fluid ports may be fluidly coupled with one or more fluid lumens extending through the shaft 28 to the handle 32. In some embodiments, the elongate medical device 24 may comprise an introducer that includes at least one lumen configured to receive another device such as a catheter or probe.

Figure 2:
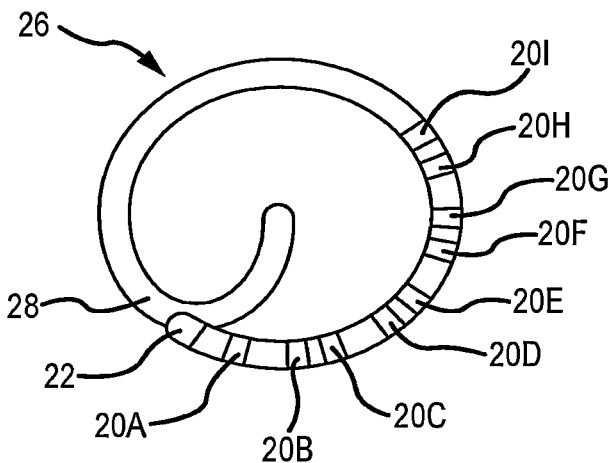
FIG. 2 is an end view of the distal end portion of the elongate medical device of FIG. 2, illustrating multiple electrodes that may be used on the device.

The distal end portion 26 of the shaft 28 of the exemplary catheter 24 may have a lariat shape. In this embodiment, the lariat shape may be formed by, for example, a shape memory wire disposed within the shaft. A tip electrode 22 and a number of ring electrodes 20A, 20B, 20C, 20D, 20E, 20F, 20G, 20H, 20I (which, may be referred to herein individually and generically as a ring electrode 20 or in the multiple as the ring electrodes 20) may be disposed on the distal end portion 26 of the shaft 28. For example, the tip electrode 22 and ring electrodes 20 may be disposed on the lariat portion of the shaft 28. In the illustrated embodiment, the distal end portion 26 includes nine (9) ring electrodes 20 (i.e., a "decapolar" catheter having ten total electrodes, as illustrated in FIG. 2). In other embodiments, the distal end portion 26 includes nineteen (19) ring electrodes 20 (i.e., a "duo-decapolar" catheter having twenty total electrodes). The electrodes 20, 22 on the catheter 24 illustrated in FIGS. 1 and 2 may be used for applying ablation energy to tissue, acquiring electrophysiology data from tissue, determining the position and orientation (P&O) of the shaft, and/or other purposes. The electrodes 20, 22 may be coupled to electrical wiring within the shaft 28, which may extend to the handle 32 and to electromechanical connectors for coupling to external systems. The ring electrodes 20 may be placed in pairs, in one non-limiting embodiment, with two electrodes 20 in a pair disposed a first distance away from each other along the length of the shaft 28, and second pair of electrodes 20 separated by a second distance along the length of the shaft 28. For example, electrodes 20B and 20C (e.g., bi-pole pair of electrodes) may be considered a first pair, electrodes 20D and 20E may be considered a second pair, and so on. These distances may be equal or the first distance may be different than the second distance. It will be appreciated that the catheter, 24 illustrated in FIGS. 1 and 2 is exemplary in nature only. The teachings of the present disclosure may find use with numerous other medical devices, such as circular mapping catheters, other known mapping and diagnostic catheters, and other known medical devices.

An elongate medical device having multiple electrodes, such as the catheter 24, may find use in a system for assessing a state of contact between the elongate medical device and the tissue of a patient. As mentioned in the Background, in some known systems, an electrical current may be driven between an electrode on an elongate medical device disposed within the body and a cutaneous electrode to assess such contact. The electric potential on the in-body electrode may be measured with reference to a third electrode (e.g., another cutaneous electrode), and an impedance may be calculated, where such an impedance may indicate a contact state. Such a uni-polar system and methodology may be improved upon by a system for assessing a contact state according to an electrical current driven between two electrodes on the same device (e.g., on the same elongate medical device within the patient's body). That is, impedance may be measured between a pair of electrodes (e.g., bi-pole pair of electrodes), on the same device, eliminating artifacts that may appear in a uni-polar arrangement. For instance, in a uni-polar arrangement some of the current between the internal electrode and the external electrode must pass through the lungs of a patient, which changes impedance with each breath.

Figure 3:
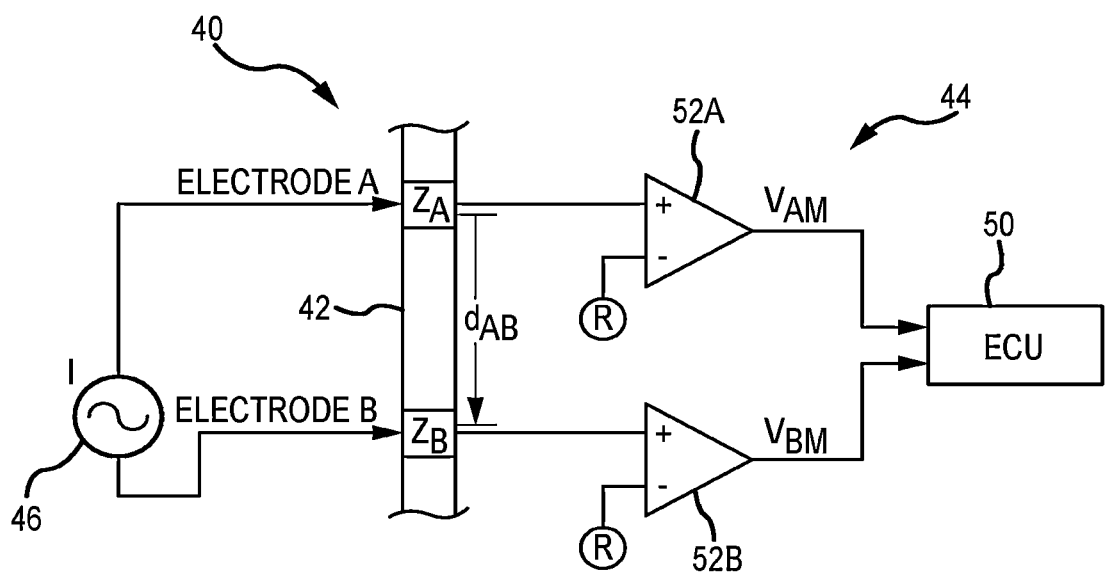
FIG. 3 is a diagrammatic view of an exemplary embodiment of a system for determining an impedance at two electrodes on an elongate medical device.

FIG. 3 is a diagrammatic view of a system 40 for assessing a contact state according to an electrical current driven between two electrodes (e.g., a bi-pole electrode) on the same device. The system 40 may include a medical device 42 comprising at least two electrodes A, B having respective impedances $Z_A$, $Z_B$, a detection amplifier 44, and a signal generator 46. The detection amplifier may include, in one non-limiting embodiment, two operational amplifiers (op amps) $52_A$, $52_B$, a reference electrode R, and a measurement circuit or impedance sensor, which may be part of an electronic control unit (ECU) 50. In one embodiment, the signal generator may be incorporated in or may be considered a part of the ECU.

The medical device 42 may be or may include an elongate medical device such as the catheter 24 (see FIG. 1). The electrodes A, B may be any two electrodes on the device. For example, referring to FIG. 2, the electrodes A, B may be the tip electrode 22 and the first ring electrode 22A. Alternatively, the electrodes A, B may be two ring electrodes 20D and 20E, or 20F and 20G, etc.

The signal generator 46 may be configured to generate (e.g., among other signals), a drive signal or excitation signal across the electrodes A, B (i.e., using one electrode as a source and the other as a sink). In one embodiment, the drive signal may have a frequency within a range from about 1 kHz to over 500 kHz, more typically within a range of about 2 kHz to 200 kHz, and even more typically about 20 kHz. In one embodiment, the drive signal may be a constant current signal, typically in the range of between 20-200 μA, and more typically about 100 μA.

The ECU 50 may include conventional filters (e.g., bandpass filters) to block frequencies that are not of interest, but permit appropriate frequencies, such as the drive frequency, to pass, as well as conventional signal processing software used to obtain the component parts of the measured complex impedance. Accordingly, the ECU 50 may include a memory storing such signal processing software and a processor configured to execute the signal processing software. The ECU 50 may include any processing apparatus such as, as noted above, a memory and a processor. Additionally or alternatively, the impedance sensor may include an application-specific integrated circuit (ASIC), programmable logic device (PLD), field-programmable gate array (FPGA), and/or other processing device.

The detection amplifier 44 may have a positive polarity connector (e.g., first channel) which may be electrically connected to a first electrode A and a negative polarity connector (e.g., second channel) which may be electrically connected to a second electrode B. The positive and negative polarity connectors may be disposed relative to the other components of the detection amplifier 44 so as to form the circuit diagrammatically shown in FIG. 3 when connected with the electrodes A, B. It should be understood that the term connectors as used herein does not imply a particular type of physical interface mechanism, but is rather broadly contemplated to represent one or more electrical nodes.

The detection amplifier may drive a current between electrodes A, B on the same device to assess a contact state between the electrodes A, B and tissue. Impedances may be calculated based on those driven currents to determine a contact state. The system may be configured to determine impedances respective of the first and second electrodes A, B to determine a contact state.

Determination of impedances may begin with driving a sinusoidal electrical signal (e.g., drive signal or excitation signal) between electrodes A and B, with one of electrodes A and B selected as a source, and the other as a sink. The source and sink selection may be made by the ECU 50, and the current driven by the signal generator 46. The drive signal may have predetermined characteristics (e.g., frequency and amplitude). Electrical potentials are measured on electrodes A and B while driving the current between electrodes A and B. The potentials may be measured by a detection amplifier, in an embodiment. The detection amplifier may present a very high impedance (for example, about 100 kW or more, in an embodiment, and/or 50 times or more greater than the nominal impedance of one of the electrodes A, B, in an embodiment, and/or 100 times or more greater than the nominal impedance of one of the electrodes A, B, in an embodiment) relative to the path between electrodes A and B, so the effect of measurements with the detection amplifier on the potential on the electrodes A, B may be negligible.

Measurement may further include referencing the measured electric potentials to a reference electrode, such as electrode R (shown in FIG. 3). Reference electrode R may be a cutaneous electrode, such as a body patch electrode, in an embodiment. Alternatively, the reference electrode R may be another in-patient electrode. Such referencing may be performed by inputting the potential on electrode A into a first input of the first op amp 52$_A$, the potential on electrode B into a first input of the second op amp 52$_B$, and the potential on the reference electrode into respective second inputs on both the first op amp 52$_A$ and the second op amp 52$_B$. The output of the op amps 52$_A$, 52$_B$ may be input to the ECU 50 for impedance determinations, contact assessment, and/or other calculations. In another embodiment, hardware separate from the ECU 50 may be provided to perform some or all of the impedance and/or contact determinations.

For driving the current between electrodes A and B and determining electric potentials on electrodes A and B, known methods of driving a current at a particular carrier frequency and demodulating the respective potentials on electrodes A and B may be used. The detection amplifier may amplify the signals manifest on each electrode A, B, and after demodulation a voltage related to the impedance of each electrode is available. In the case of electrode B, the recovered voltage will be negative (i.e., assuming electrode A is selected as the source and B as the sink), so a conversion to a positive quantity may be applied by the ECU 50 or other device. Since the current source-sink electrode pair may comprise a closely spaced bi-pole, the potential at the reference electrode R with respect to the bi-pole will be similar, and thus the physical location of R may vary with little effect on the voltages between A and R and B and R.

For a given electrode geometry for which impedance is measured at a sufficiently high frequency, the potential measured for a current driven between electrodes A, B may be essentially resistive in a pure saline or blood medium, and may reflect the electrode's geometry and the solution conductivity. For example, a spherical electrode in a homogenous medium will have an electric potential for a current driven through the electrode according to equation (1) below:

$$V = \frac{\rho I}{4\pi r} \quad (1)$$

where V is the electric potential, I is the applied current, $\rho$ is the media resistivity, and r is the distance from the center of the electrode at which the potential measurement is made. The measured impedance may be taken as the measured potential on the electrode divided by the applied current, as set forth in equation (2) below:

$$Z = \frac{V}{I} \quad (2)$$

Calculation of impedance based on electrode geometry is well known. Along these lines, equations for ring electrodes and/or conversions from a spherical electrode to a ring electrode are known. Further, the effect of the influence of one electrode (e.g., A) on another electrode (e.g., B) of and electrode pair can be calculated and accounted for. Exemplary embodiments for calculating impedance based on electrode geometry and accounting for effects of influence of an adjacent electrode are described, for example only, in U.S. patent application publication no. 2014/0364715, hereby incorporated by reference in its entirety.

For each potential measured while a current is driven between electrodes A and B, geometry specific equations may be solved (e.g., by the ECU 12) to determine the voltages on each of electrodes A and B (relative to reference electrode R). Accordingly, such equations may be stored in the memory of the ECU 50 for execution by the processor of the ECU 50. Those voltages may then be applied to equation (1) or another geometric specific equation to determine impedances respective of each of electrode A and B (again, by the ECU 50, for example). Based on those impedances, a contact state between electrodes A and B and the tissue of a patient may be assessed. Such measurements may be carried out numerous times. Furthermore, such measurements may be carried out for numerous sets of electrodes A and B. That is, impedance potentials may be carried out repeatedly for numerous different pairs of electrodes to determine a contact state for each of those electrodes. For example, referring to FIGS. 1 and 2, the measurements may first be carried out on electrodes 22 and 20A, then on 20B and 20C, then on 20D and 20E, and so on. Stated otherwise, the impedance of pairs of electrodes may be determined sequentially.

While contact assessments based on a current driven between electrode pairs on a catheter (or other medical device) provides increased accuracy in comparison to contact assessments based on a current driven between an electrode on a catheter and an exterior/cutaneous electrode, aspects of the present disclosure are based, in part, on the realization that previous contact assessment systems have limitations. One specific limitation is that medical standards establish current limits (auxiliary current) for medical devices. For instance, such industry standards allow for 10 micro-amps of current for an intra-cardiac electrode for AC currents below 1 kHz. At 10 kHz, the limit is 100 micro-amps with proportionally increasing limits with increasing frequency (i.e., at 20 kHz the limit is 200 micro-amps). The auxiliary current limitation (e.g., threshold) works against a current trend in electrode catheters. Namely, the increasing number of electrodes carried on a catheter (or other medical device) to improve, for example, mapping accuracy and/or ablation control. By way of example, one existing electrode catheter, the FIRMmap basket catheter by Topera/Abbott Laboratories, utilizes 64 separate electrodes. Other proposed catheters contain 100 or even 200 separate electrodes. FIG.

4 illustrates a distal end of an exemplary catheter 16 having 128 electrodes. $20_1$-$20_{128}$. In the illustrated embodiment, the distal end of the catheter 16 is formed as an expandable basket having eight arm 18a-h. The arms 18a-h may be formed of shape metal wires such that they expand to the illustrated shape when disposed through the end of, for example, an introducer. Each arm includes 16 electrodes forming 8 pairs of electrodes. In the case of such a 128 electrode catheter, impedance of 64 electrode pairs may be sequentially determined. Such sequential determination of such a large number of electrode pairs reduces the response time of the system. Another solution is to simultaneously the drive current across each pair of electrodes. However, if the electrodes pair are driven with a current at a common or single frequency, cross talk between the electrode pairs makes identifying the response of any given pair of electrodes difficult or impossible. Additionally, driving a current across a plurality of electrode pairs at a single frequency results in additive auxiliary current (e.g., at a surface electrode or other internal electrode). For instance, for an auxiliary current limit of 100 micro-amps (e.g., excitation frequency at 10 kHz), a catheter having 20 bi-pole electrodes (i.e., forty channels; 20 pairs of electrodes) would be limited to using a 5 micro-amp current (i.e., 20 bi-poles*5 micro-amps=100 micro-amps). The sum current is an additive total of all of the channels. For a catheter having 100 pairs of electrodes (e.g., bi-poles), the drive current would be limited to 1.0 micro-amps. As the number of electrodes increases, the magnitude of the drive current must decrease to maintain the sum current below threshold auxiliary current limits. As will be appreciated, lowering the magnitude of the drive current applied across each bi-pole reduces the signal-to-noise ratio of its response. Accordingly, for medical devices with high numbers of electrodes, the response of the bi-pole pairs of electrodes may be overwhelmed by noise.

Aspects of the present disclosure are further based on the recognition that utilization of multiple drive signals having multiple different frequencies (e.g., unique frequencies) allows for increasing the magnitude of the drive current for each pair of electrodes (e.g., bi-pole) or increasing the number of bi-poles without exceeding auxiliary current limits/thresholds. That is, it has been recognized that the sum current where multiple bi-poles are excited by multiple drive signals each having different/unique frequencies rises with the square root of the number of channels. In such a configuration, the total measured current or sum current is:

$$Itotal = Ifrequency * \sqrt{Nfrequencies} = Ifrequency * \sqrt{\left(\frac{Nchannels}{2}\right)} \quad (3)$$

Where Ifrequency is the current per frequency (i.e., per bi-pole electrode pair) and Nfrequencies is the total number of frequencies. Note the total number of channels is twice the number of frequencies (since one frequency services a bi-pole electrode pair). For example, for a medical device or catheter having 200 electrodes, 100 different frequencies would be used. Assuming these frequencies are above 10 kHz (e.g., spaced every 25 Hz over a 2500 Hz band 15-17.5 kHz), drive signals having a 5 micro-amp current would result in a sum current of no more than 50 micro-amps (i.e., 5 micro-amps*√100), well below the 100 micro-amp limit for 10 kHz. Of note, for the actual safe current limit is greater than 100 micro-amps as each additional frequency is higher than previous and thus greater than 10 kHz. However, the 100 micro-amp limit is utilized for simplicity.

Figure 5:
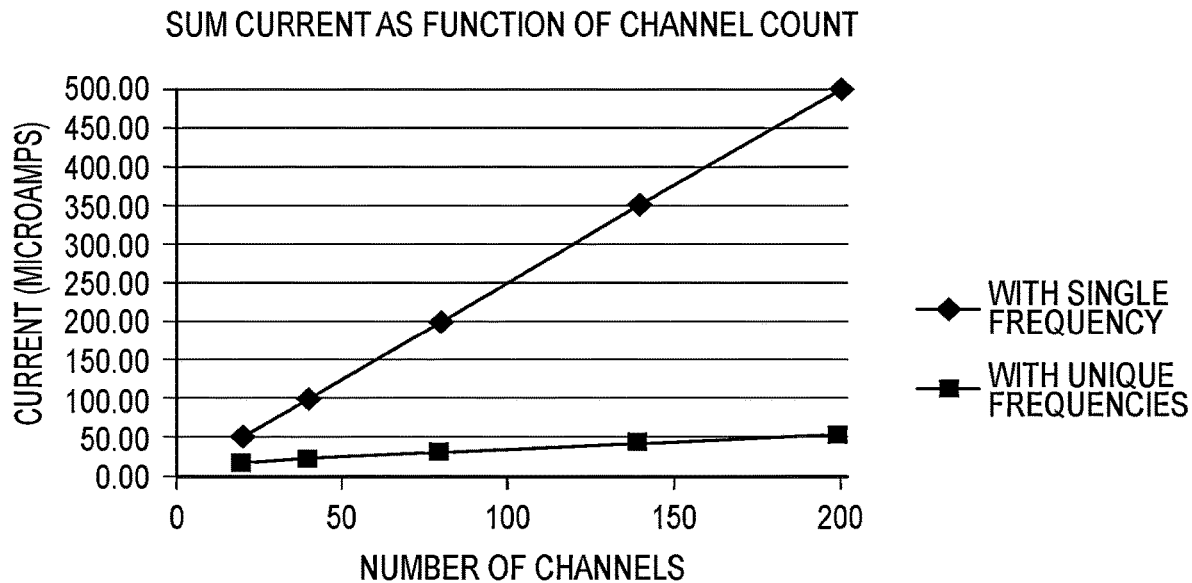
FIG. 5 is a chart illustrating a sum current as a function of channel count.

The reduction of the sum current resulting from use of multiple unique frequencies compared to the single frequency example discussed above (i.e., 100 bi-poles; 1 micro-amp drive current; 100 micro-amp sum current) occurs in conjunction with a five-fold increase in the magnitude of the drive current (i.e., 5 micro-amps vs. 1 micro-amp). This is illustrated in the chart of FIG. 5. As the chart demonstrates, the application of a single frequency drive signal with a 5 micro-amp drive current, 100 micro-amps is reached at 40 channels (e.g., 20 bi-pole at 5 micro-amps each) while only 50 micro-amps is reached at 200 channels when using unique frequencies. The use of unique frequencies provides a significant advantage in increasing the total number of electrode for a medical device.

Equation (3) may be rearranged to find the maximum number of channels for a given drive current:

$$Nchannels = 2\left(\frac{Itotal}{Ifrequency}\right)^2 \quad (4)$$

Thus, with 5 micro-amps per bi-pole at 10 kHz and higher (using a flat 100 micro-amp auxiliary limit/threshold for simplicity) the maximum number of channels is:

$$2\left(\frac{100 \text{ uA}}{5 \text{ uA}}\right)^2 = 2(20^2) = 800 \text{ channels} \quad (5)$$

Figure 6:
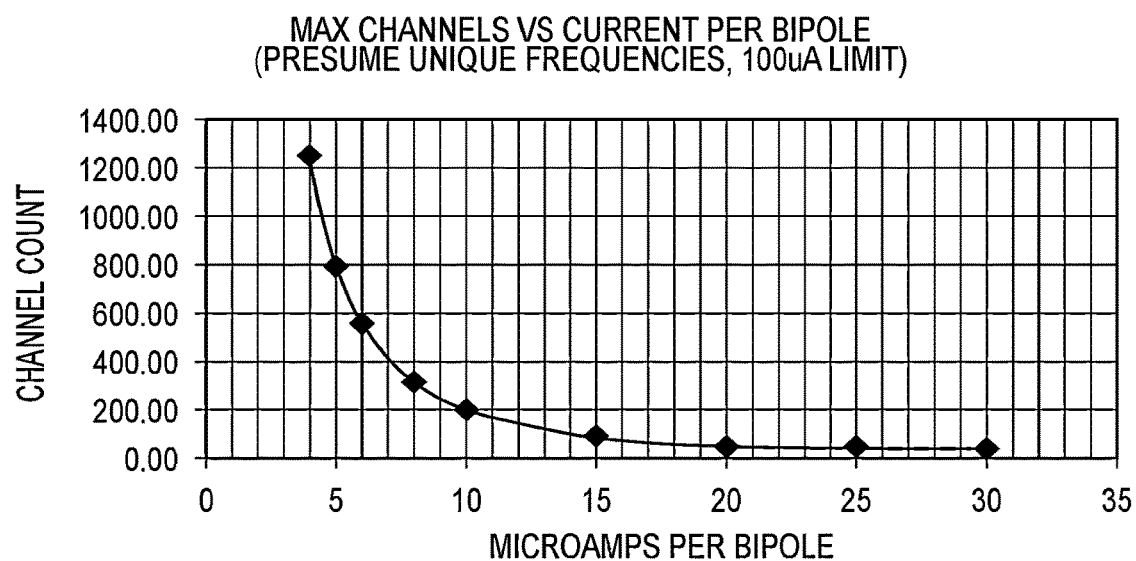
FIG. 6 is a chart illustrating a maximum number of channels vs. current.

Conversely, doubling the current per bi-pole electrode pairs reduces the maximum number of channels as a function of its square. That is, when using a 10 micro-amp drive signal per bi-pole, 200 channels would be allowed. When using a 20 micro-amp drive signal per bi-pole, 50 channels would be allowed. Stated otherwise, lowering current increases allowable channel count by a square factor while increasing current decreases allowable channel count by a square factor. FIG. 6 provides a chart that illustrates how a 100 uA limit can be achieved with different current levels per bi-pole and associated channel count. As shown, below about 15 micro-amps the number of allowable channels increases dramatically. This demonstrates the advantage of reducing the current per bi-pole. Of further note, this also allows determining a maximum drive current based on a number of bi-poles contained on or in a medical device. That is, the drive current may be maximized for a given number of bi-poles while remaining within safe sum current limits to enhance signal-to-noise ratios of response signals.

Higher unique frequencies also assist in increasing the maximum number of channels possible while maintaining safe sum current limits. For a 200 micro-amp auxiliary current limit (e.g., for frequencies 20 kHz and up), the theoretical count increases to:

$$2\left(\frac{200 \text{ uA}}{5 \text{ uA}}\right)^2 = 2(40^2) = 3200 \text{ channels} \quad (6)$$

Such a large number of channels may not be practical for many reasons but demonstrates the benefit of higher frequencies along with low drive current per bi-pole pair. In any arrangement, use of unique frequencies for the drive signals of a plurality of bi-pole electrodes significantly increases the number of bi-poles that may be interrogated to determine impedance. Alternatively, use of unique frequencies allows for increasing the magnitude of a drive current applied to the bi-poles while maintaining auxiliary current limits for a patient below a predetermined threshold.

While utilizing unique frequencies for each drive signal provides significant benefits for determining impedances of high count electrode medical devices, the measured response signal to the drive signals must be identified for each bi-pole. The disclosed method and system utilizes digital signal processing to synchronously demodulate the response signal (e.g., voltage signal) at each electrode. Another important aspect of the present disclosure is that driving each electrode pair/bi-pole at a unique frequency not only allows for significantly increasing a number of electrodes that may be interrogated and/or increasing drive current magnitudes but also minimizes crosstalk between channels.

The following discussion, is directed to an exemplary embodiment of a medical device having 200 electrodes (100 bi-poles) using 100 spaced drive frequencies. By spacing these drive frequencies at exactly 25 hertz apart, the bandwidth requirement is 25×100=2500 hertz. Other frequency offsets are possible. In this example drive frequencies from 15025 Hz through 17500 are utilized. Keeping the frequencies tightly packed simplifies bandwidth requirements of the digitizing amplifier circuit. Further, each electrode pair/bi-pole is driven with a current in the 1 to 10 micro-amp range. It will be appreciated that different frequency ranges and drive currant ranges may be utilized.

Synchronous demodulation allows the unique frequencies to be detected independent of each other while minimizing crosstalk. To achieve this, the drive frequencies are made orthogonal to each other by setting the drive frequencies at harmonics of a base frequency (e.g., 25 Hz in the present example) and measuring a response over a period with an integer number of cycles. By selecting an update/sampling rate of 25 per second (e.g., 40 millisecond period), frequencies on 25 hertz boundaries will have integer number of cycles in each sampling period. That is, frequencies on 25 hertz boundaries such as 16025, 16050, 16075 hertz etc. will be orthogonal to each other. The sampling rate of 25 per second was selected as a compromise between tight frequency packing and fast response time. For cardiac application, it is noted that a heart beats in the range of 1 to 4 beats per second and 25 samples per second is capable of tracking changes due to cardiac motion. It is possible to space frequencies closer together, but the ability to track impedance change through the cardiac cycle diminishes. Reducing the spacing by a factor of 2 to 12.5 Hz would also reduce the reporting/sampling rate to 12.5 per second and, while possible, is less than ideal for tracking the impedance changes in a rapidly beating heart. Likewise, it is possible to increase spacing and, in turn, achieve more samples per second, though bandwidth requirements increase.

Synchronous demodulation consists of multiplying the measured and digitized response signal (which is a composite of multiple frequencies) by a replica of each drive signal of exactly the same frequency and a known phase offset. The resultant signal is then low-pass filtered and decimated to (in this example) 25 samples per second. The sampling rate of the analog-to digital converter (ADC) is not critical and in fact need not meet the traditional Nyquist sampling rate. However, the amplifying circuit must have adequate bandwidth to pass the signal to the ADC. By calibrating the system and compensating for expected phase delay between drive signal and received signal, quadrature demodulation may occur. Thus, a real component for resistive impedance and an imaginary component for reactive impedance may be found. This is commonly known as complex impedance. Synchronous demodulation also allows for signal extraction with very low current levels. Successful detection of impedance below 1 micro-amp has been demonstrated, though higher current levels provide better signal-to-noise ratio.

Figure 7:
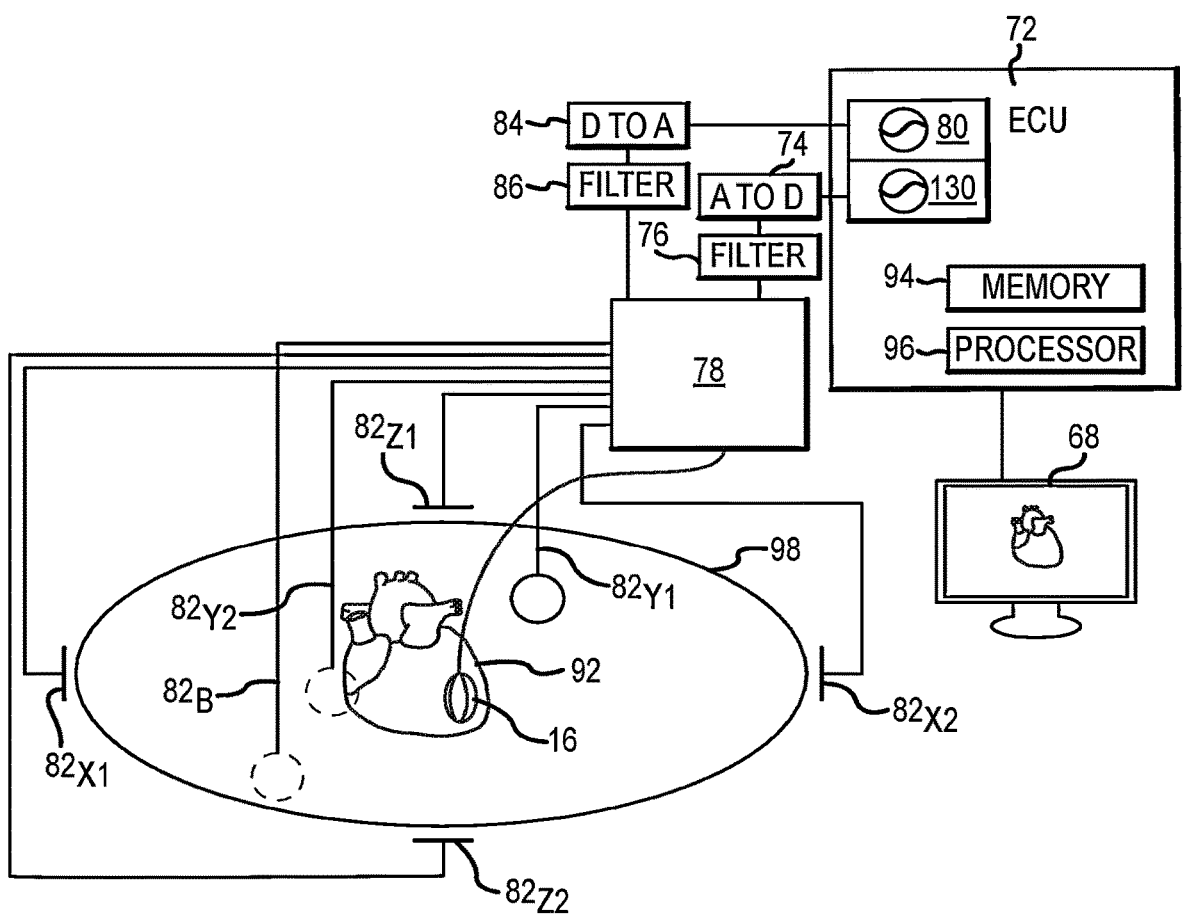
FIG. 7 is a diagrammatic depiction of an exemplary system that may include functionality for determining impedances for a plurality of pairs of electrodes on an elongate medical device.

FIG. 7 is a diagrammatic depiction of an embodiment of an exemplary mapping and navigation system 70 that be utilized with an elongated medical device 16 to, for example, determine impedance, determine contact sensing, determine the location (i.e., position and orientation) of an elongate medical device (e.g., catheter) within the body of a patient, map the anatomy of the patient, etc. The system 70 may include various visualization, mapping and navigation components as known in the art, including, for example, an EnSite™ Velocity™ system commercially available from St. Jude Medical, Inc., or as seen generally, for example, by reference to U.S. Pat. No. 7,263,397, or U.S. patent application publication no. 2007/0060833, both of which are hereby incorporated by reference in their entireties as though fully set forth herein.

Figure 4:
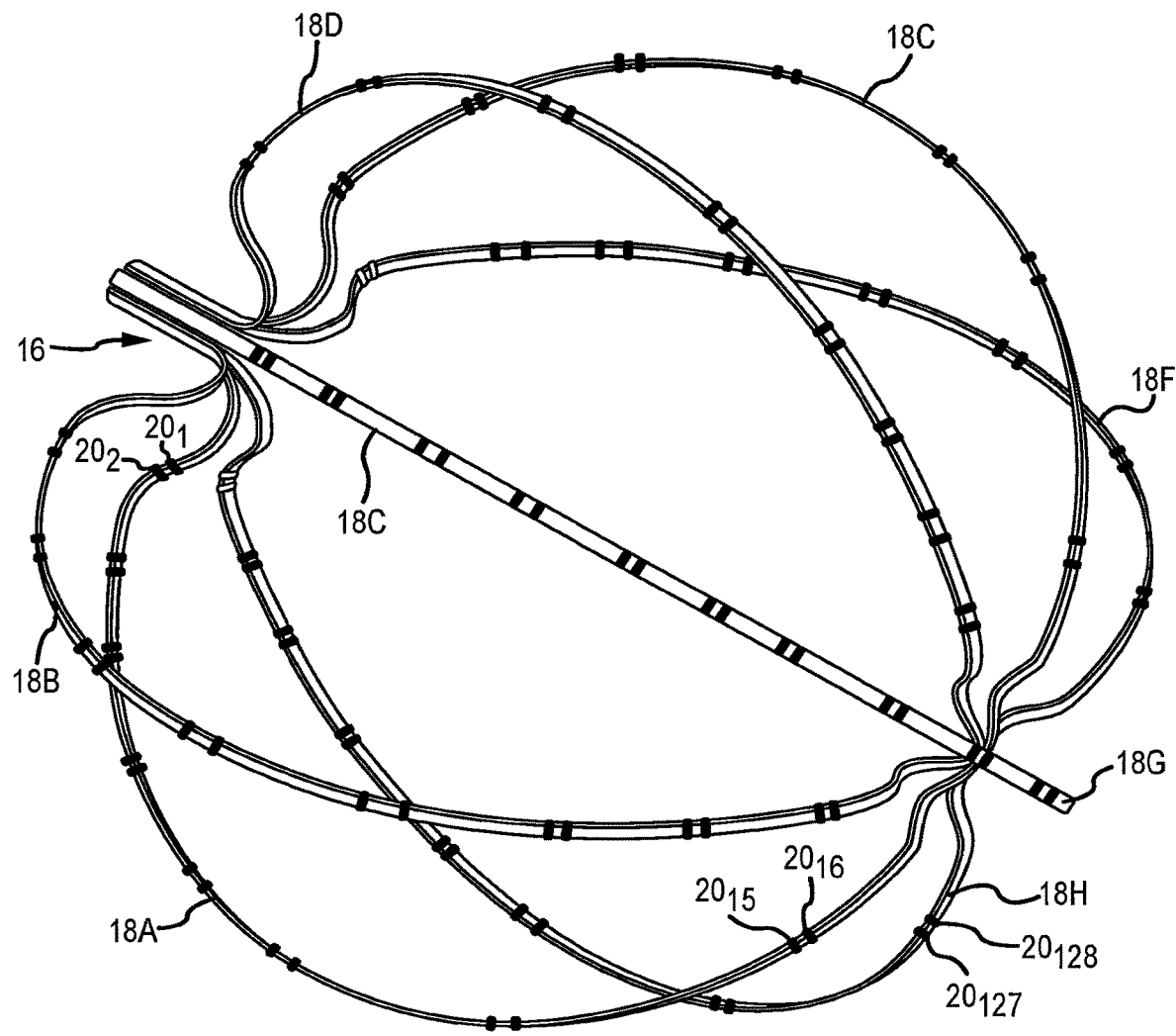
FIG. 4 is an end view of a distal end portion of an alternate embodiment of an elongate medical device illustrating a high electrode count.

The system 70 may include an electronic control unit (ECU) 72, an analog-to-digital converter (A-to-D) 74, a filter 76 (e.g., bandpass filter), a digital to analog converter 84, a filter 86 (e.g., bandpass filter), a switch 78, a signal source or signal generator 80, a demodulator circuit 130, a graphical user interface 68 and, in various embodiments, a plurality of body surface patch electrodes 82. Additional circuitry may be included as more fully discussed below. The system 70 may be electronically and/or mechanically coupled with an elongate medical device such as the 128 electrode catheter 16 of FIG. 4. The system 70 may be configured for a number of functions for guiding the elongate medical device 16 to a target site within the body of a patient 98, such as the heart 92, and for assessing contact between the elongate medical device 84 and the tissue of the patient 98. The elongate medical device may be one of the catheters 24 or 16 described herein (see FIGS. 1 and 4), or some other elongate medical device. The elongate medical device may have a plurality of pairs of electrodes.

The signal generator 80 outputs multiple excitation or drive signals for assessing an impedance of one or more electrodes. More specifically, the signal generator 80 may generate a plurality of excitation or drive signals having unique frequencies within a range from about 1 kHz to over 500 kHz, more typically within a range of about 2 kHz to 200 kHz, and even more typically between about 10 kHz and about 20 kHz, in one embodiment. The drive signals may each have a constant current, typically in the range of between 1-200 µA, and more typically about 5 µA, in one embodiment. The signal generator 80 may also generate signals involved in, for example, determining a location of the electrodes 92 within the body of the patient.

The ECU 72 may include a memory 94 and a processor 96. The memory 94 may be configured to store data respective of the elongate medical device 84, the patient 98, and/or other data (e.g., calibration data). Such data may be known before a medical procedure (medical device specific data, number of catheter electrodes, etc.), or may be determined and stored during a procedure. The memory 94 may also be configured to store instructions that, when executed by the processor 96, cause the ECU 72 to perform one or more methods, steps, functions, or algorithms described herein. For example, but without limitation, the memory 94 may include data and instructions for determining impedances respective of one or more electrodes 92 on the elongate medical device 84. The ECU may be connected to a graphical user interface 68, which may display an output of sensed tissue (e.g., heart), the elongated medical device (not shown)

and/or assessed values (e.g., impedances) for electrodes of the elongated medical device.

Figure 8:
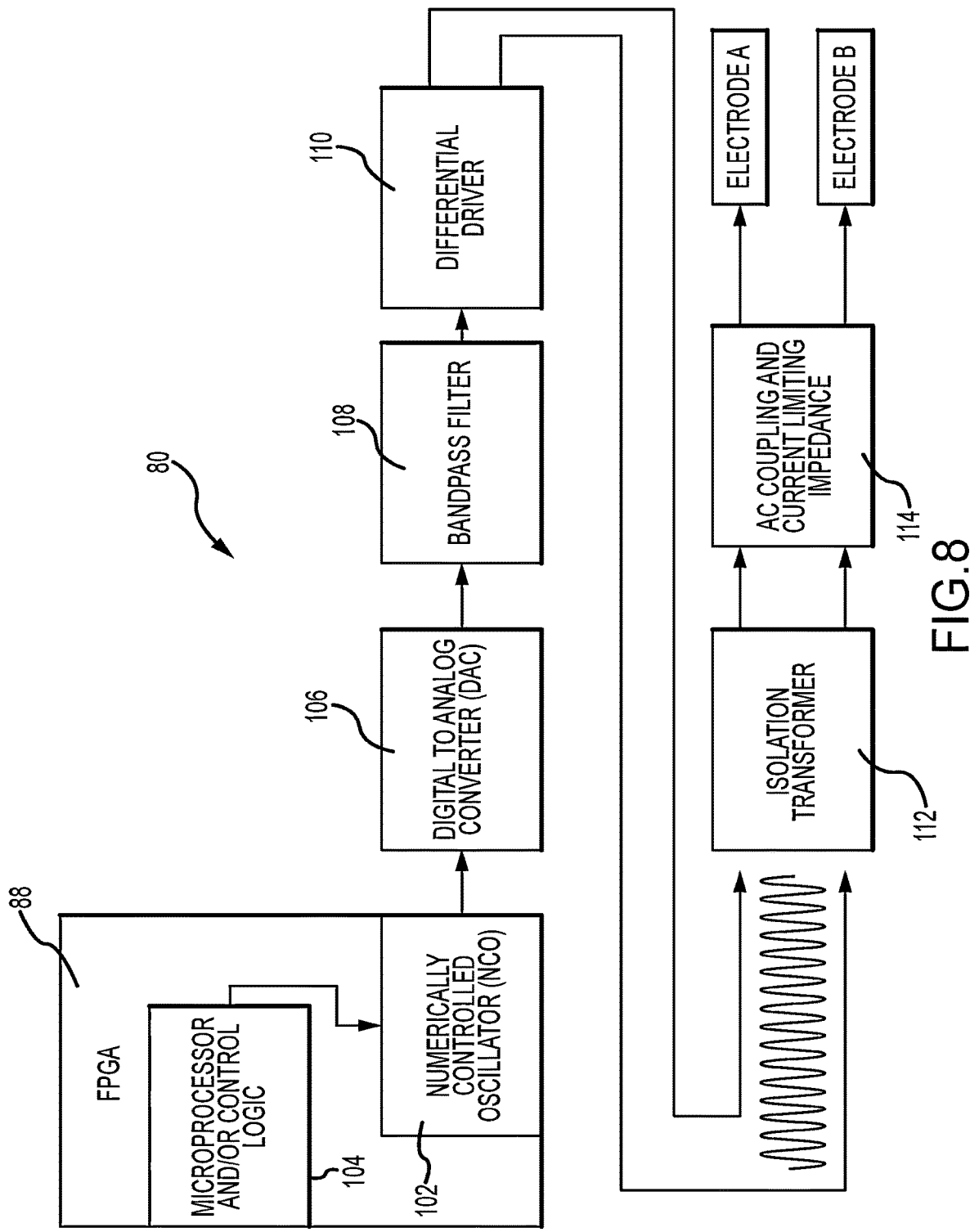
FIG. 8 is a diagrammatic depiction of one embodiment of a current source.

FIG. 8 illustrates one embodiment of a signal source 80 (e.g., current source) that provides an excitation signal for one pair of electrodes. In the present embodiment, the signal source 80 includes a field programmable gate array (FPGA) 88. However, it will be appreciated that other circuitry, including without limitation, application specific integrated chips, Altera Cyclone series or Xilinx Spartan series may be utilized. In the present embodiment, the FPGA 88 includes a numerically controlled oscillator (NCO) 102. The NCO 102 is a digital signal generator which creates a synchronous (i.e. clocked), discrete-time, discrete-valued representation of a waveform, usually sinusoidal. The NCO 102 is programmable to provide a waveform having a desired frequency, amplitude and/or phase.

In the present embodiment, the NCO 102 creates a sinusoidal waveform of a desired frequency based on an input (e.g., single fixed-frequency reference) provided from a microprocessor and/or control logic 104. In the present embodiment a microprocessor/control logic 104 is incorporated in the FPGA provides the inputs to the NCO 102. However, it will be appreciated that the NCO inputs may be provided by, for example, the processor 96 of the ECU 72. In any arrangement, the NCO 102 generates a digital waveform output having a desired frequency (e.g., unique frequency). The output of the NCO is received by a digital to analog converter (DAC) 106, which converts the received digital signal to a corresponding analog signal. A bandpass filter 108 is utilized to smooth the converted analog signal. A differential driver (e.g., op amp) 110 receives the smoothed analog signal from the bandpass filter 108 and sends the same signal as a differential pair of signals, each in its own conductor to an isolation transformer 112. Provided that impedances in the differential signaling circuit (e.g., differential driver and isolation transformer) are equal, external electromagnetic interference tends to affect both conductors identically. As the receiving circuit (isolation transformer) only detects the difference between the conductors, the technique resists electromagnetic noise compared to a one conductor arrangement. The isolation transformer 112 transfers AC current of the signals originating from the source 80 to the electrodes A and B of the medical device while isolating the medical device from the source. The isolation transformer 112 blocks transmission of DC components in the signals from passing to the electrodes while allowing AC components in signals to pass. The dual output from the isolation transformer 112 is received by AC coupler 114 (e.g., capacitor) that further limits low frequency current from passing to the electrodes. The AC coupler outputs the signals to the electrodes A and B of the electrode pair (e.g., bi-pole). The AC coupler 114 has an impedance that is orders of magnitude greater than the impedance across the electrodes A and B.

Figure 9:
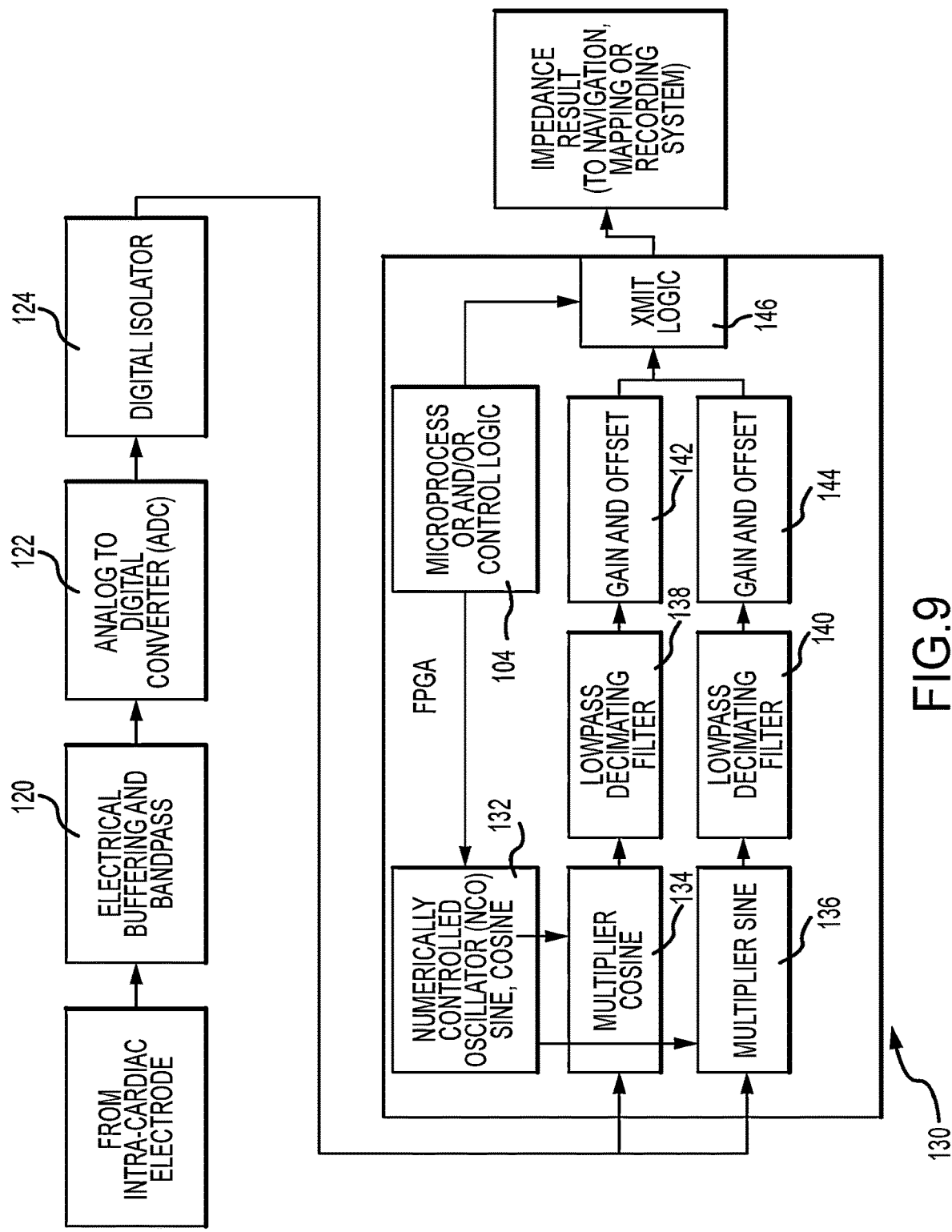
FIG. 9 is a diagrammatic depiction of one embodiment of a measurement circuit and demodulation circuit.

FIG. 9 illustrates one embodiment of a signal measuring circuit (e.g., signal sampler) and a synchronous demodulation circuit. Initially, a response signal from one of the electrodes A or B is received at a filter 120 (e.g., buffer amplifier) that transfers a current from the electrode, which has a low output impedance level, to an analog to digital converter (ADC) 122, which typically has a high input impedance level. The buffer amplifier prevents the second ADC from loading the current of electrode circuit and interfering with its desired operation. The ADC 122 samples the received analog signal at a known sampling rate (e.g., 64 k/s) and converts the analog response signal to a digital response signal. In the present embodiment, an output of the ADC passes through a digital isolator 124, which transfers the digital response signal to the control system (e.g., ECU) while isolating the control system from the medical device.

The digital response signal passes to a synchronous demodulator circuit 130 which, in the present embodiment, is defined in the same FPGA utilized for the signal source 80. As noted, synchronous demodulation consists of multiplying a digitized response signal by a replica of a drive signal of exactly the same frequency and a known phase offset. That is, a demodulation signal having the same frequency as the drive signal and a known phase offset from the drive signal is generated and multiplied with the digitized response signal. Generating the demodulation signal(s) using the same FPGA 88 that generates the drive signal(s) simplifies the demodulation process. However, it will be appreciated that this is not a requirement and that the synchronous demodulator circuit and the signal source may be separate and/or formed of different software and/or hardware components. In any arrangement, the synchronous demodulation circuit must be able to replicate the drive signal for a given frequency.

In the illustrated embodiment, the digital response signal is split as it is received by the synchronous demodulator circuit 130. A numerically controlled oscillator (NCO) 132 generates sine and cosine representations of the drive signal (e.g., same frequency different phase) based on an input provided from the microprocessor and/or control logic 104. The split digital response signals are multiplied point-by-point by the sine and cosine signals in sine and cosine multipliers 134, 136, respectively. This yields a real (sine) and an imaginary (cosine) channel. The sine and cosine channels are filtered and decimated by low pass decimating filters 138, 140, which in the present embodiment are formed of cascaded integrator-comb (CIC) filters. Following the example above, where the drive signal is a harmonic of a 25 Hz base frequency, the channels/signals are decimated to 25 samples per second such that each decimated signal has an integer number of cycles. The decimated signals then pass through a gain and offset calibration 142, 144 to compensate for expected phase delays between the source signal and the response signal. The signals may then be combined. That is, quadrature demodulation may occur. Thus a real component of resistive impedance and an imaginary component of reactive impedance may be found. This information may then be transmitted, for example, via an output port 146 to, for example, the ECU. The above noted measuring and demodulation process may be performed for the responses of both electrodes A and B.

Figure 10:
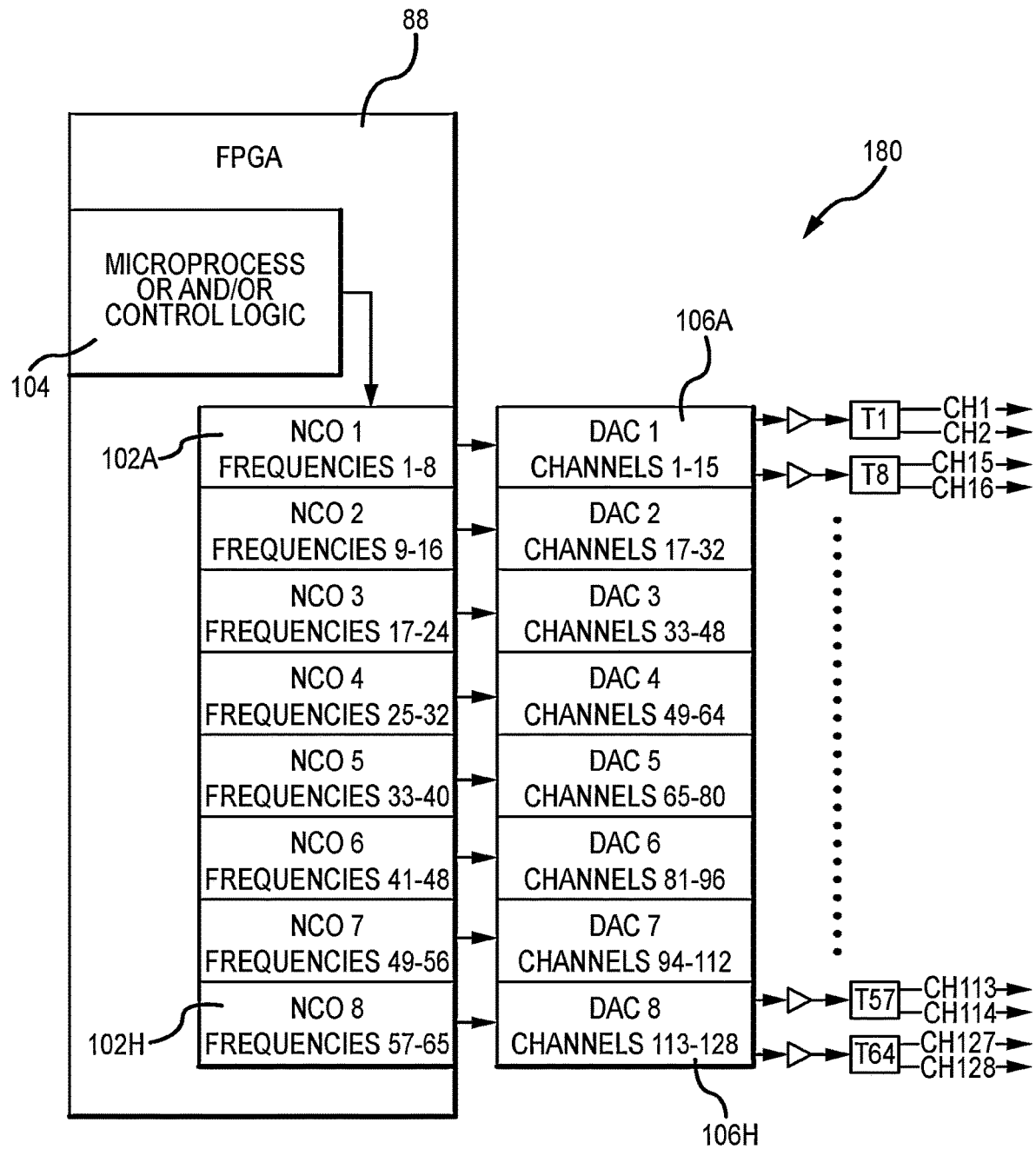
FIG. 10 is a diagrammatic depiction of an embodiment of a current source configured to provide a plurality of drive signals to electrodes of a medical device.

In order to accommodate a plurality of electrodes, the systems and processes of FIGS. 8 and 9 may be scaled. FIG. 10 illustrates an embodiment of a signal source 80 (e.g., current source) scaled to provide a plurality of unique frequency excitation/drive signals for a plurality of electrode pairs/bi-poles. In the illustrated embodiment, the current source 80 provides 64 unique frequencies to 128 total electrodes (i.e., 64 electrode pairs/bi-poles). It will be appreciated that this embodiment is provided by way of example and not by way of limitation. Along these lines, unique frequency drive signals may be provided for more or fewer frequencies and/or electrodes. Similar to the signal source described above in relation to FIG. 8, the signal source 80 is defined within a field programmable gate array (FPGA) 88. The FPGA 88 further includes a plurality of numerically controlled oscillators (NCOs) 102a-h (hereafter NCO 102 unless specifically referenced). As above, the NCOs 102 receive a reference signal input from a micro-compressor and/or control logic 104. In the illustrated embodiment, each NCO 102 has eight channels. That is, each NCO 102 is programmable to provide eight unique frequencies. In this regard, the eight NCOs 102*a-h* are operative to provide 64 unique frequencies. Continuing with the previous example, each NCO provides eight unique frequencies spaced on 25 Hz intervals. Collectively, the NCOs 102*a-h* provide 64 individual frequencies between approximately 16 kHz and 18 kHz. The output of each NCO 102 is received by a digital to analog converter (DAC) 106*a-h*. Each DAC has eight independent channels each configured to generate an analog representation of a received drive signal frequency for receipt by the electrodes of an attached medical device. Similar to the source described in relation to FIG. 8, the output of the DAC's may be received by bandpass filters, differential drivers and/or transformers prior to being applied to individual electrodes of the medical device.

Figure 11:
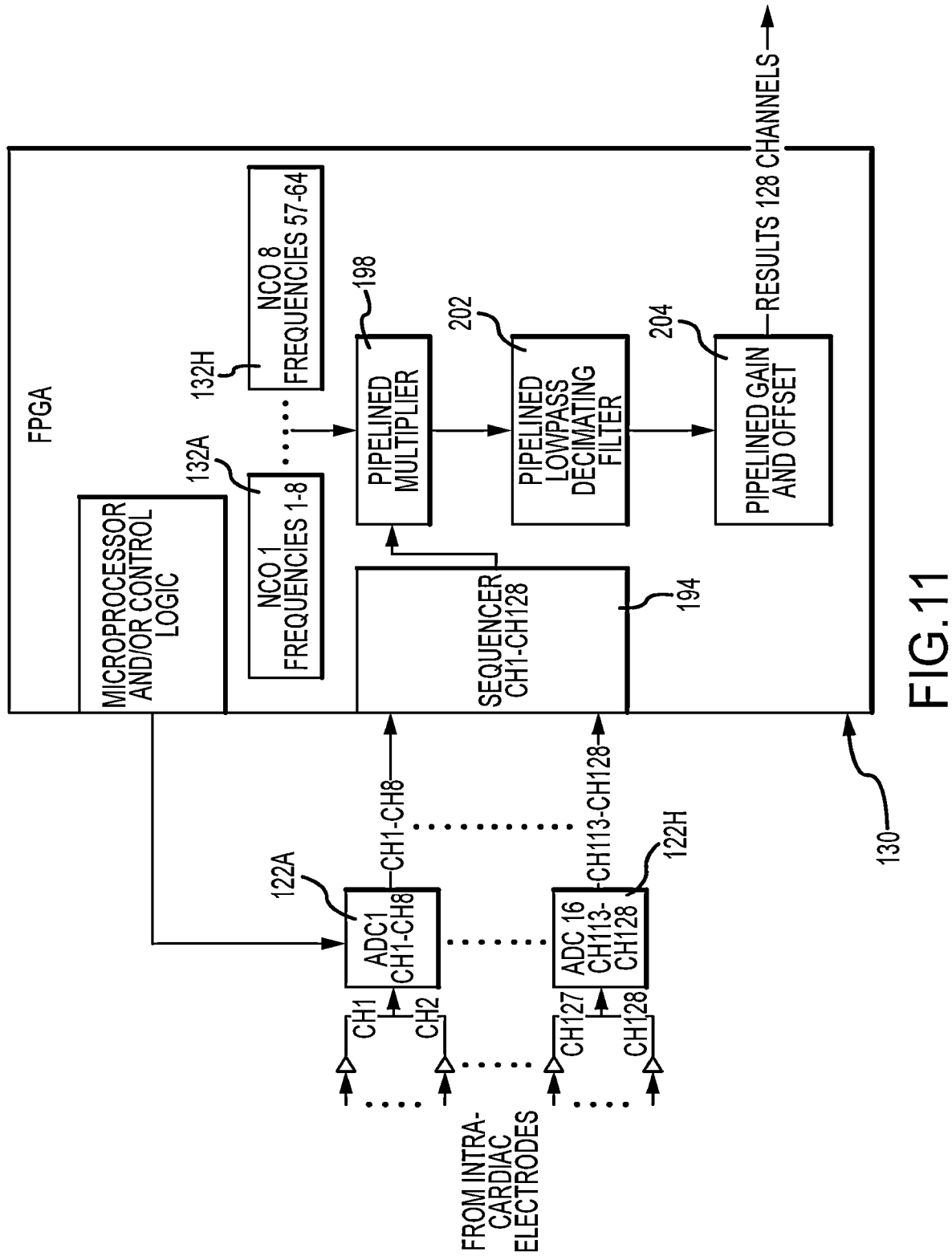
FIG. 11 is a diagrammatic depiction of an embodiment of a measurement circuit and demodulation circuit configured to measure and demodulate responses from a plurality of electrodes of a medical device.

FIG. 11 illustrates one embodiment of a multi-channel signal measuring circuit and multi-channel synchronous demodulation circuit. The overall operation of the embodiment of FIG. 11 is similar to the operation of the embodiment of FIG. 9. Initially, response signals from the electrodes are received at a filter (e.g., buffer amplifier) that transfers a current from the electrodes to analog to digital converters (ADCs) 122*a-h* (hereafter 122 unless specifically referenced). As with the DAC's of the signal source, the measurement circuit utilizes eight ADCs each of which receives eight unique frequencies from 16 attached electrodes. That is, each ADC services eight channels with simultaneous sampling of all channels. The ADCs 122 sample the received analog signals (e.g., eight channels) at a known sampling rate (e.g., 64 k/s) and converts the analog responses of the electrodes to digital response signals.

A synchronous demodulator circuit 130 receives the digital response signals from the ADCs 122. In the present embodiment, the synchronous demodulator circuit 130 is defined in the same FPGA utilized for the signal source 80. More specifically, the digital signals are received by a 128 channel sequencer 194 which samples all the signals at one point time and provides the sampled signals to a pipelined multiplier 198. The pipelined multiplier is in communication with a plurality of NCOs 132*a-h*, which again generate appropriately phase delayed sine and cosine representations of each unique frequency drive signal based on inputs from the microprocessor and/or control logic 104. The pipelined multiplier 198 operates in a manner that is substantially identical to the multipliers described above in relation to FIG. 9 with the exception that pipelining allows the calculations of all channels to run concurrently. The pipelined multiplier 198 multiplies each response by sine and cosine demodulation signals. The output of the pipeline multiplier 198 is provided to a pipelined low pass decimating filter 202, which samples the outputs over an integral number of cycles, as described above. The decimated signals then pass through pipelined gain and offset calibration 204 to convert to units of ohms impedance. Thus a real component of resistive impedance and an imaginary component of reactive impedance may be found for each of the 128 electrodes. This information may then be transmitted to the ECU.

Figure 12:
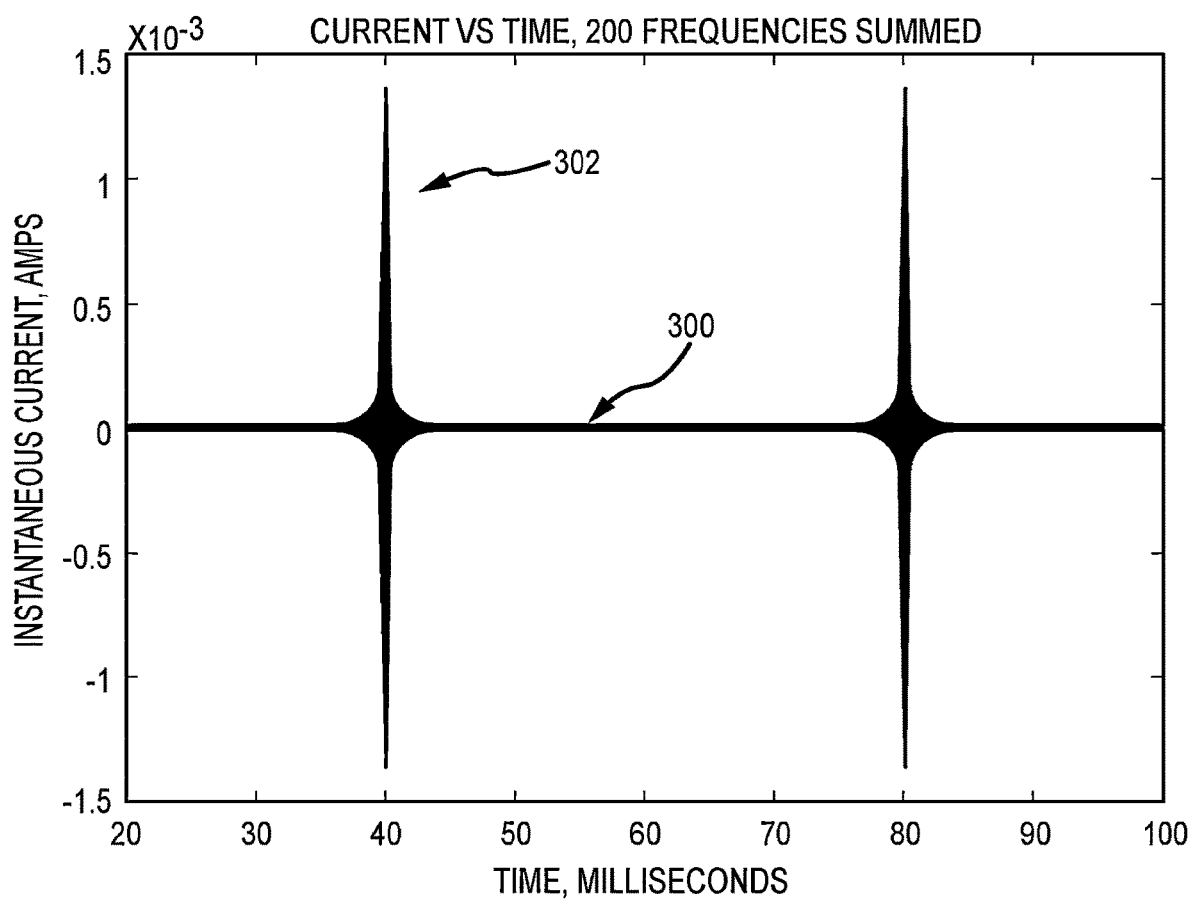
FIG. 12 is a chart illustrating a sum current of a plurality of harmonic frequencies.

The systems and processes of FIGS. 8-11 allow for synchronous demodulation of a large number of electrodes when the drive signals are orthogonal (i.e., unique drive frequencies at harmonics of a base frequency and responses are measured over a period with an integer number of cycles). Further, the use of multiple unique drive frequencies allow increasing the drive current as the RMS (root mean square) value of the resultant signal increases with the square root of the number of channels. What is not obvious is the signals may add in a manner that creates a large peak value periodically when all the frequencies come into phase. One aspect of the synchronous demodulation scheme is the frequencies are not random, but are chosen to be separated by a fixed amount. As such, if all the frequencies start at time zero and are on 25 Hz boundaries (or other equal boundaries), every 40 milliseconds (25 times per second) all signals will be nearly in phase and a large instantaneous peak value results. This is shown graphically in FIG. 12 which shows a trace of a sum current 300 where 200 frequencies starting at 16025 Hz and every 25 Hz thereafter to 19500 Hz are added together. Mathematically, the RMS current in this case of 200 frequencies at 5 micro-amps is (5×4200) or about 70 micro-amps. However, there is a peak 302 in the sum current 300 of about 1 milliamp every 40 milliseconds. Such a peak current would be expected to exceed an auxiliary current limit/thresholds. This can be countered by adding a random (non-uniform) phase offset to each channel. This minimizes the peaking and spreads the current over time. The sum current 400 with each channel assigned a random phase, is illustrated in FIG. 13.

Figure 13:
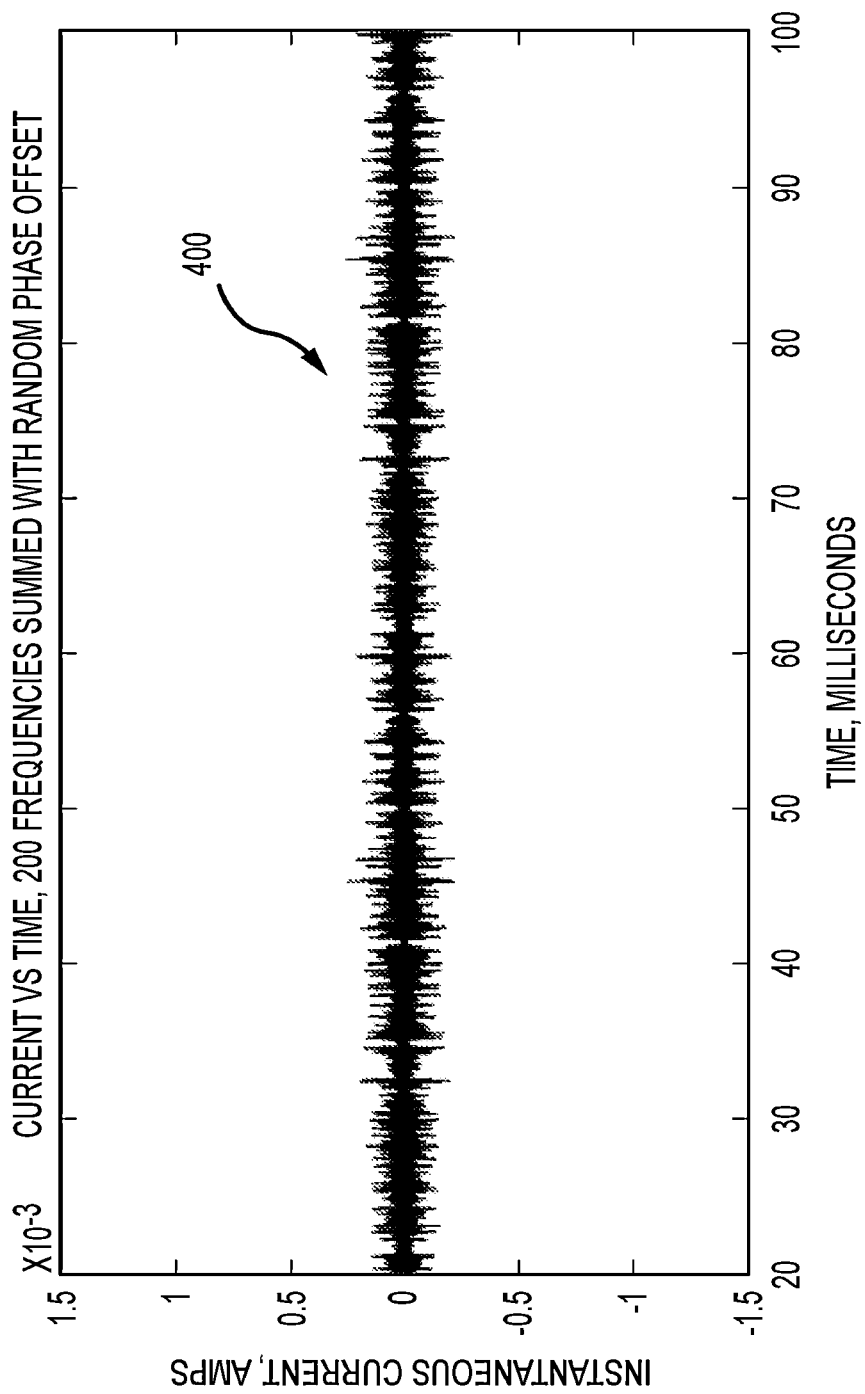
FIG. 13 is a chart illustrating a sum current when a plurality of harmonic frequencies have random phase offsets.

As shown in FIG. 13, when random phase offsets are applied to each drive signal, the sum current 400 is much more uniform and lower in peak current. The addition of phase offset to each frequency of the drive signals does not hinder the synchronous demodulation as the drive signals remain orthogonal at 25 Hz apart. The phase offset is compensated during demodulation by simply phase delaying each input (e.g., reference frequency) in the FPGA as necessary at calibration time. This is facilitated by the use of separate NCOs for the signal source and demodulation circuit, which have both frequency and phase inputs. The source NCOs are assigned a one-time random phase offset that may be stored by the ECU and/or the FPGA. The demodulation NCOs are assigned a respective phase offset during a one-time calibration that compensates for the source NCO phase offset plus any phase delay between source NCO 102 and analog-to-digital convertor 122. Said calibration data is likewise stored by the ECU and/or FPGA.

Figure 14:
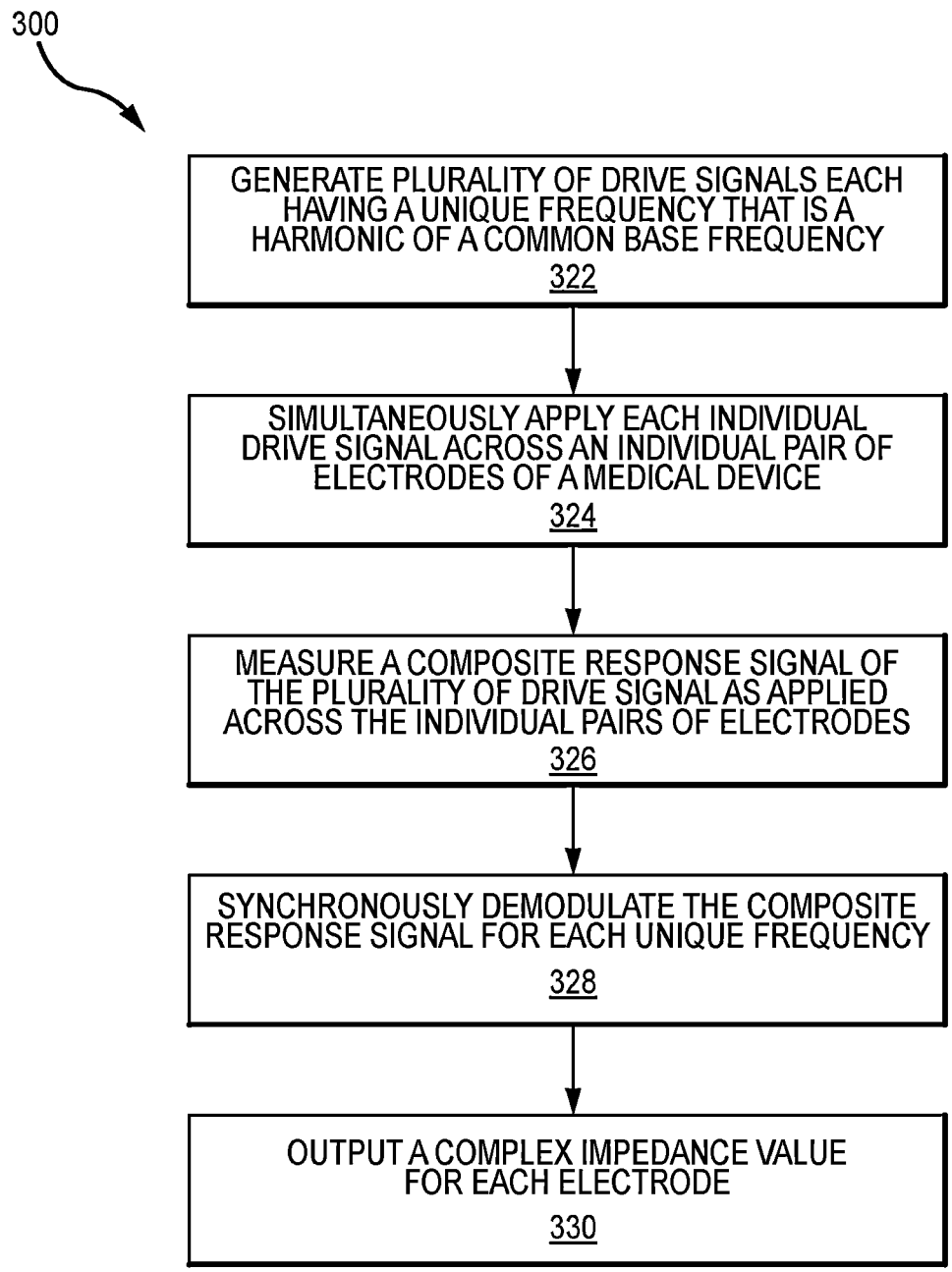
FIG. 14 is a flow chart illustrating a process for use with the disclosed systems.

FIG. 14 illustrates a process 320 that may be performed by the systems described above. Initially, the process includes generating 322 a plurality of drive signals each having a unique frequency that is a harmonic of a common base frequency. The generation of such a plurality of drive signals may further entail assigning each drive signal a random phase offset. Such random phase offsets may be predetermined. Once the drive signals are generated, the drive signals are simultaneously applied 324 across individual pairs of electrodes of a medical device. The application of the drive signals may further include digital to analog conversion of the drive signals prior to their application to the electrodes. One or more composite response(s) of the electrodes to the drive signals is measured 326. The measurement may further entail converting analog responses of the electrodes to digital signals. The digital signals are then synchronously demodulated 328. The synchronous demodulation entails generating demodulation signals for each unique frequency. Each demodulation signal will have the same frequency and a known phase offset for a corresponding drive signal. If each drive signal has a random phase offset, the corresponding to modulation signals will have the same random phase offset. The synchronous demodulation of the drive signals may also include sampling the signals over a time period that includes an integer number of cycles for the drive signals. The synchronous demodulation outputs 330 a complex impedance value for each electrode. That is, a real impedance value and a reactive impedance value may be output for each electrode. For instance, these outputs may be output to the graphical user interface 68 (see FIG. 7). Along these lines, the assessed value for each electrode may be displayed on the graphical user interface 68 along with a graphical depiction of the catheter to provide a user with feedback on the contact status of each electrode. That is, the impedance values may be utilized for, among other things, to assess electrode contact with tissue.

Figure 15:
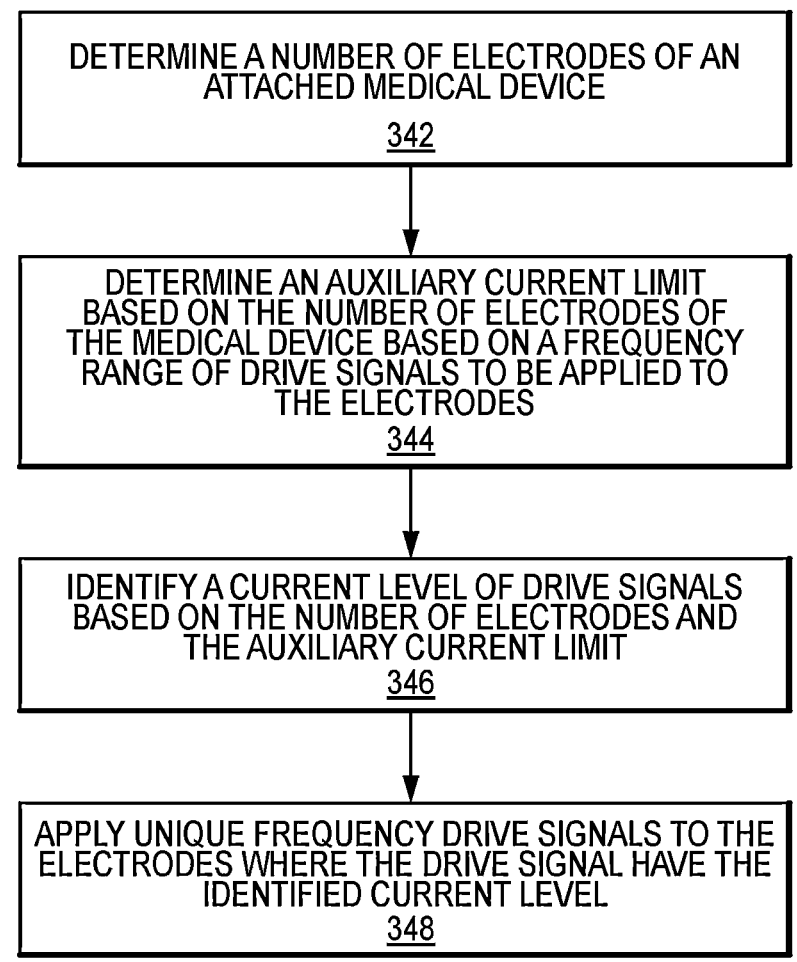
FIG. 15 is a flow chart illustrating another process for use with the disclosed systems.

FIG. 15 illustrates a further process 340 that may be performed by the systems described above. The process allows for dynamically adjusting current levels of drive signals applied to a plurality of electrodes of a medical device. Initially, the process includes determining 342 a number of electrodes of an attached medical device. Such determination may be performed by a control unit (e.g., ECU) interrogating the attached medical device. Alternatively, a system user may input this information. Based on the number of electrodes and a frequency band for a plurality drive signals that will be applied to the electrodes, an auxiliary current limit or threshold is determined 344. The auxiliary current limit may be determined from stored data (e.g., calibration data). Based on the auxiliary current limit and the number of electrodes, a current level may be identified 346 for drive signals that will be applied to electrodes. For instance, the current level of the drive signals may be maximized to enhance the signal-to-noise response of the signals when applied to the electrodes while maintaining a sum current of the drive signals below the auxiliary current limit. Once the current level for the drive signals is identified, unique frequency drive signals are applied 348 to the electrodes where each drive signal has identified current level.

The systems described above provides further benefits for use with medical devices. For instance, utilization of the DACs to generate the drive signals provides a means for deactivating a channel. In this regard, simply setting a DAC to zero or a static value effectively turns off a channel. Along these lines, channels may be purposefully deactivated to permit increased current levels for drive signals if needed. Another benefit is provided by the bandpass filters. As the bandpass filters only permit passage of a narrow frequency and/or amplitude signal, any software or hardware errors that result in outputting a drive signal of excessive magnitude is not passed. The bandpass filters provide a fail-safe limit to the drive signals.

In addition to impedance calculations and contact state determinations, the system 70 may be configured to determine the position and orientation (P&O) of an elongate medical device 16 (e.g., of a distal end portion of a catheter) within the body of the patient 98. Accordingly, the ECU 72 may be configured to control generation of one or more electrical fields and determine the position of one or more electrodes 92 within those fields. The ECU 72 may thus be configured to control signal generator 80 in accordance with predetermined strategies to selectively energize various pairs (dipoles) of body surface patch electrodes 82 and catheter electrodes.

Referring again to FIG. 7, a mapping and navigation functionality of the system 70 will be briefly described. The body surface patch electrodes 82 may be used to generate axes-specific electric fields within the body of the patient 98, and more specifically within the heart 92. Three sets of patch electrodes may be provided: (1) electrodes $82_{X1}$, $82_{X2}$, (X-axis); (2) electrodes $82_{Y1}$, $82_{Y2}$, (Y-axis); and (3) electrodes $82_{Z1}$, $82_{Z2}$, (Z-axis). Additionally, a body surface electrode ("belly patch") $82_B$, may be provided as an electrical reference. The body patch electrodes $82_{X1}$, $82_{X2}$, $82_{Y1}$, $82_{Y2}$, $82_{Z1}$, $82_{Z2}$, $82_B$ may be referred to herein generically as a body patch electrode 82 or as the body patch electrodes 82. Other surface electrode configurations and combinations are suitable for use with the present disclosure, including fewer body patch electrodes 82, more body patch electrodes 82, or different physical arrangements, e.g. a linear arrangement instead of an orthogonal arrangement.

Each patch electrode 82 may be independently coupled to the switch 78, and pairs of patch electrodes 82 may be selected by software running on the ECU 72 to couple the patch electrodes 82 to the signal generator 80. A pair of electrodes, for example the Z-axis electrodes $82_{Z1}$, $82_{Z2}$, may be excited by the signal generator 80 to generate an electrical field in the body of the patient 86 and, more particularly, within the heart 88. In an embodiment, this electrode excitation process occurs rapidly and sequentially as different sets of patch electrodes 82 are selected and one or more of the unexcited surface electrodes 82 are used to measure voltages. During the delivery of the excitation signal (e.g., current pulse), the remaining (unexcited) patch electrodes 82 may be referenced to the belly patch $82_B$ and the voltages impressed on these remaining electrodes 82 may be measured. In this fashion, the patch electrodes 82 may be divided into driven and non-driven electrode sets. A low pass filter may process the voltage measurements. The filtered voltage measurements may be transformed to digital data by the analog to digital converter and transmitted to the ECU 72 for storage (e.g. in the memory 94) under the direction of software. This collection of voltage measurements may be referred to herein as the "patch data." The software may store and have access to each individual voltage measurement made at each surface electrode 82 during each excitation of each pair of surface electrodes 82.

Generally, in an embodiment, three nominally orthogonal electric fields may be generated by the series of driven and sensed electric dipoles in order to determine the location of the elongate medical device 16 (i.e., of one or more electrodes). Alternately, these orthogonal fields can be decomposed and any pair of surface electrodes (e.g., non-orthogonal) may be driven as dipoles to provide effective electrode triangulation.

The patch data may be used, along with measurements made at one or more electrodes catheter electrode and measurements made at other electrodes and devices, to determine a relative location of the one or more catheter electrodes. In some embodiments, electric potentials across each of the six orthogonal patch electrodes 82 may be acquired for all samples except when a particular surface electrode pair is driven. In an embodiment, sampling electric potentials may occur at all patch electrodes 82, even those being driven.

As a part of determining locations of various electrodes, the ECU 72 may be configured to perform one or more compensation and adjustment functions, such as motion compensation. Motion compensation may include, for example, compensation for respiration-induced patient body movement, as described in U.S. patent application publication no. 2012/0172702, which is hereby incorporated by reference in its entirety.

Data sets from each of the patch electrodes 82 and the catheter electrodes are all used to determine the location of the catheter electrodes within the patient 98. After the voltage measurements are made for a particular set of driven patch electrodes 82, a different pair of patch electrodes 82 may be excited by the signal generator 80 and the voltage measurement process of the remaining patch electrodes 82 and catheter electrodes takes place. The sequence may occur rapidly, e.g., on the order of 100 times per second in an embodiment. The voltage on the catheter electrodes within the patient 98 may bear a linear relationship with the position of the electrodes between the patch electrodes 82 that establish the electrical fields, as more fully described in U.S. Pat. No. 7,263,397, which is hereby incorporated by reference in its entirety.

In summary, FIG. 7 shows an exemplary system 70 that employs seven body patch electrodes 82, which may be used for injecting current and sensing resultant voltages. Current may be driven between two patches 82 at any time. Positioning measurements may be performed between a non-driven patch 82 and, for example, belly patch 82$_B$ as a ground reference. The position of an electrode 92 may be determined by driving current between different sets of patches and measuring one or more impedances. Some impedances that may be measured may be according to currents driven between pairs or sets of two catheter electrodes on the elongate medical device 16. In one embodiment, time division multiplexing may be used to drive and measure all quantities of interest. Position determining procedures are described in more detail in, for example, U.S. Pat. No. 7,263,397 and publication no. 2007/0060833 referred to above.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

Although numerous embodiments have been described above with a certain degree of particularity, those skilled in the art could make numerous alterations to the disclosed embodiments without departing from the spirit or scope of this disclosure. For instance, the present disclosure discusses a bi-pole configuration where each pair of electrodes is independent of all other pairs of electrodes. However, another possibility is to configure electrodes such that one side of each bi-pole is a common electrode. For example, with reference to the catheter of FIG. 2, the tip electrode 22 may form a common electrode for each of the additional ring electrodes 20A-I. That is, tip electrode 22 may be one electrode of each pair of electrodes.

All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the any aspect of the disclosure. As used herein, the phrased "configured to," "configured for," and similar phrases indicate that the subject device, apparatus, or system is designed and/or constructed (e.g., through appropriate hardware, software, and/or components) to fulfill one or more specific object purposes, not that the subject device, apparatus, or system is merely capable of performing the object purpose. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method comprising:
   generating a plurality of drive signals each having a unique modulation frequency that is a harmonic of a common base frequency;
   simultaneously applying the plurality of drive signals to a plurality of electrode pairs, wherein a different drive signal of the plurality of drive signals is applied to each electrode pair;
   measuring a composite response signal from signals produced by simultaneous application of the plurality of drive signals to the plurality of electrode pairs,
   synchronously demodulating the composite response signal to generate real impedance signals and reactive impedance signals,
      wherein synchronously demodulating the composite response signal comprises:
      generating first signals representing a real component of each signal of the composite response signal;
      generating second signals representing an imaginary component of each signal of the composite response signal; and
      generating integrated first signals and integrated second signals; and generating a complex impedance value from the real impedance signals and the reactive impedance signals.

2. The method of claim 1, further comprising compensating for a phase delay from a phase of each unique modulation frequency.

3. The method of claim 1, wherein the simultaneous application of the plurality of drive signals is to a plurality of electrodes carried by a medical device, the method further comprising:
determining an auxiliary current limit based on a number of the plurality of electrodes; and
determining a frequency band for each of the plurality of drive signals.

4. The method of claim 3, identifying a current level for each of the plurality of drive signals based on the number of the plurality of electrodes and the auxiliary current limit, wherein each of the plurality of drive signals has the identified current level.

5. The method of claim 1, wherein generating the plurality of drive signals includes introducing a random phase offset into each of the plurality of drive signals, and each demodulated signal has a same random phase offset as a corresponding drive signal.

6. An electronic control unit comprising:
a signal generator configured to generate drive signals each having a unique modulation frequency that is a harmonic of a common base frequency;
a measurement circuit for measuring a composite response signal from signals produced in response to simultaneous application of the drive signals; and
a synchronous demodulation circuit configured to generate real impedance signals and reactive impedance signals, wherein generating the real impedance signals and the reactive impedance signals comprises:
generating first signals representing a real component of each signal of the composite response signal;
generating second signals representing an imaginary component of each signal of the composite response signal; and
generating integrated first signals and integrated second signals; and
output the real impedance signals and the reactive impedance signals.

7. The electronic control unit of claim 6, wherein the synchronous demodulation circuit is configured to split each composite response signal into two channels as the composite response signal is received, the synchronous demodulation circuit comprising;
a sine multiplier for generating the first signals in one of the two channels; and
a cosine multiplier for generating the second signals in the other of the two channels.

8. The electronic control unit of claim 6, wherein the synchronous demodulation circuit comprises a plurality of first components for integrating the first signals and the second signals.

9. The electronic control unit of claim 8, wherein generating the real impedance signals and the reactive impedance signals further comprises:
downsampling the integrated first signals and the second signals to generate real impedance signals and reactive impedance signals, wherein each demodulated signal real impedance signals has a same frequency as a corresponding drive signal and each reactive impedance signals has a same frequency as a corresponding drive signal,
wherein the synchronous demodulation circuit further comprises second components configured to downsample the integrated first and second signals.

10. The electronic control unit of claim 9, wherein the first components and second components are components of a plurality of cascaded integrator-comb (CIC) filters.

11. The electronic control unit of claim 6, wherein the signal generator comprises at least one differential signaling circuit configured to receive input from at least one digital to analog converter (DAC).

12. The electronic control unit of claim 11, the signal generator further comprising at least one current limiter configured to receive output from the at least one differential signaling circuit and to output the drive signals.

13. The electronic control unit of claim 6, further comprising a multi-channel measurement circuit, and wherein the demodulation circuit is a multi-channel circuit.

14. The electronic control unit of claim 13, wherein the multi-channel measurement circuit comprises one or more multi-channel analog to digital converters (ADCs) each configured to simultaneously sample a respective subset of signals of the composite response signal.

15. The electronic control unit of claim 10, wherein the synchronous demodulation circuit is further configured to compensate for phase delays between the drive signals and the composite response signal.

16. The electronic control unit of claim 6, wherein the synchronous demodulation circuit comprises a pipelined multiplier configured to generate the first signals and the second signals.

17. A method comprising:
generating a plurality of drive signals each having a unique frequency that is a harmonic of a common base frequency;
measuring a composite response signal from signals produced by simultaneous application of the plurality of drive signals to a plurality of electrodes,
generating demodulated signals from the composite response signal, wherein the demodulated signals comprise real impedance signals and reactive impedance signals, wherein each demodulated signal has a same frequency as a corresponding drive signal; and
generating complex impedance values from the real impedance signals and the reactive impedance signals.

18. The method of claim 1, wherein synchronously demodulating the composite response signal further comprises:
downsampling the integrated first signals and the integrated second signals to generate real impedance signals and reactive impedance signals,
wherein each demodulated signal has a same frequency as a corresponding drive signal of the plurality of drive signals.

19. The electronic control unit of claim 6, wherein the signal generator is further configured to assign a random phase offset to each drive signal and each demodulated signal has a same random phase offset as a corresponding drive signal.

20. The method of claim 17, wherein each drive signal includes a random phase offset and each demodulated signal has as same random phase offset as a corresponding drive signal.

* * * * *